US006338723B1

(12) United States Patent
Carpenter et al.

(10) Patent No.: US 6,338,723 B1
(45) Date of Patent: Jan. 15, 2002

(54) COMPRESSION DEVICE WITH COMPRESSION MEASURING SYSTEM

(75) Inventors: Todd Alan Carpenter, San Diego; Sandra Anne Shaw, Coronado; James Pope, San Diego, all of CA (US)

(73) Assignee: Circaid Medical Produts, Inc., San Diego, CA (US)

( * ) Notice: Subject to any disclaimer, the term of this patent is extended or adjusted under 35 U.S.C. 154(b) by 0 days.

(21) Appl. No.: 09/398,324

(22) Filed: Sep. 16, 1999

Related U.S. Application Data
(60) Provisional application No. 60/100,511, filed on Sep. 16, 1998.

(51) Int. Cl.$^7$ ................................................ A61F 13/00
(52) U.S. Cl. ........................... 602/75; 602/60; 602/62
(58) Field of Search ........................... 602/75, 76, 77, 602/60, 61; 606/201, 202, 203; 128/869, 870, 876, 877, 878, 882

(56) References Cited

U.S. PATENT DOCUMENTS

| | | |
|---|---|---|
| 3,298,366 A | 1/1967 | Moore et al. |
| 3,538,914 A | 11/1970 | Meyers ........................ 123/165 |
| 3,613,679 A | 10/1971 | Bijou |

(List continued on next page.)

FOREIGN PATENT DOCUMENTS

| WO | WO 97/39709 | 10/1997 | ........... A61F/13/06 |
|---|---|---|---|
| WO | WO 99/36019 | 7/1999 | ........... A61F/13/08 |

OTHER PUBLICATIONS

Callam, M.J. et al., "Hazards of compression treatment of the leg: an estimate from Scottish surgeons," British Medical Journal, vol. 295, Nov. 28, 1987.

Stemmer, R., "Ambulatory elasto–compressive treatment of the lower extremities particularly with elastic stockings," Sonderdruck "Der Kassenartz" Mittellungsblatt des Deutschen Kassenarztverbandes, 1969 (pp. 1–8).

Husni, E.A., "Elastic Support of the Lower Limb, Use and Abuse," Hospital Medicine, Dec. 1971 (pp. 36–43).

Primary Examiner—Kim M. Lewis
(74) Attorney, Agent, or Firm—The Brotman Group, PC.; Harris F. Brotman

(57) ABSTRACT

A device is provided for compression of objects such as parts of the body. The device has the form of a band that can be shaped like a sleeve, wrap or garment that is sized to encircle the body part or other compressible object and having a component or components made of an elastic material. Indicia such as tick marks or scales are printed on the device. The stretch of the elastic material as the device is tensioned around the body part causes increased separation of the indicia or movement of a free end of the band with respect to the indicia. A system measures the separation of the indicia and converts it to compression as a function of the circumference of the body part. The system may be a card having edges with measurement scales or the scales may be printed on the device and the displacement of a free end of a band or sub-band of the device with respect to the scales indicates the compression for particular circumferences of the body part. The device may have additional scales printed on it for measuring the circumference of the body part.

58 Claims, 25 Drawing Sheets

U.S. PATENT DOCUMENTS

| | | |
|---|---|---|
| 3,628,536 A | 12/1971 | Glesne |
| 3,845,769 A | 11/1974 | Shaw |
| 3,856,008 A | 12/1974 | Fowler et al. |
| 4,133,307 A | 1/1979 | Ness |
| 4,213,463 A | 7/1980 | Osenkarski ................. 128/639 |
| 4,215,687 A | 8/1980 | Shaw |
| 4,243,039 A | 1/1981 | Aginsky |
| 4,437,408 A | 3/1984 | Arkans ....................... 101/426 |
| 4,502,301 A | 3/1985 | Swallow et al. .............. 66/178 |
| 4,513,740 A | 4/1985 | Westlake ................... 128/165 |
| 4,770,175 A | 9/1988 | McEwen |
| 5,048,536 A | 9/1991 | McEwen |
| 5,111,806 A | 5/1992 | Travis ......................... 602/19 |
| 5,120,300 A | 6/1992 | Shaw ........................... 602/61 |
| 5,195,950 A | 3/1993 | Delannoy .................... 602/75 |
| 5,254,122 A | 10/1993 | Shaw ......................... 606/201 |
| 5,425,702 A | 6/1995 | Carn et al. .................... 602/62 |
| 5,501,060 A | 3/1996 | Weder et al. ................. 53/399 |
| 5,503,620 A | 4/1996 | Danzger ..................... 602/19 |
| 5,653,244 A | 8/1997 | Shaw ......................... 128/882 |

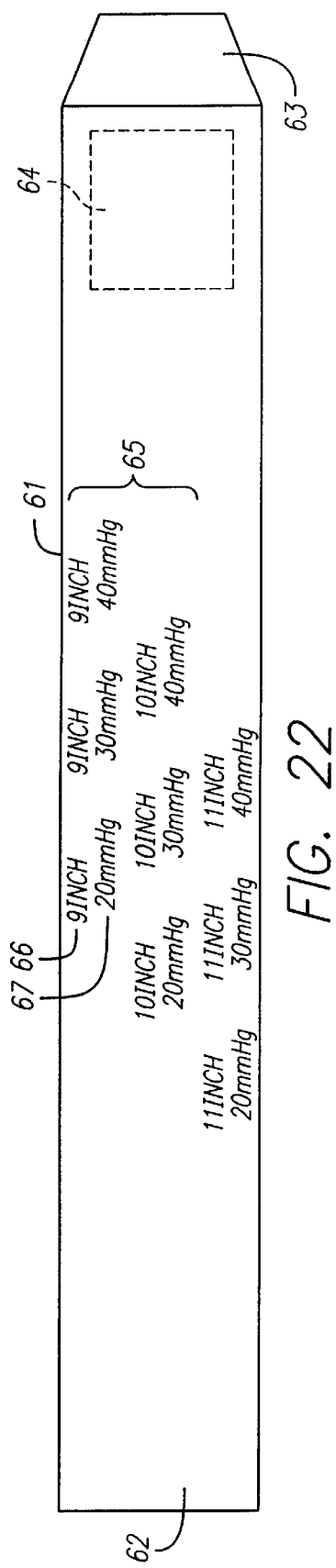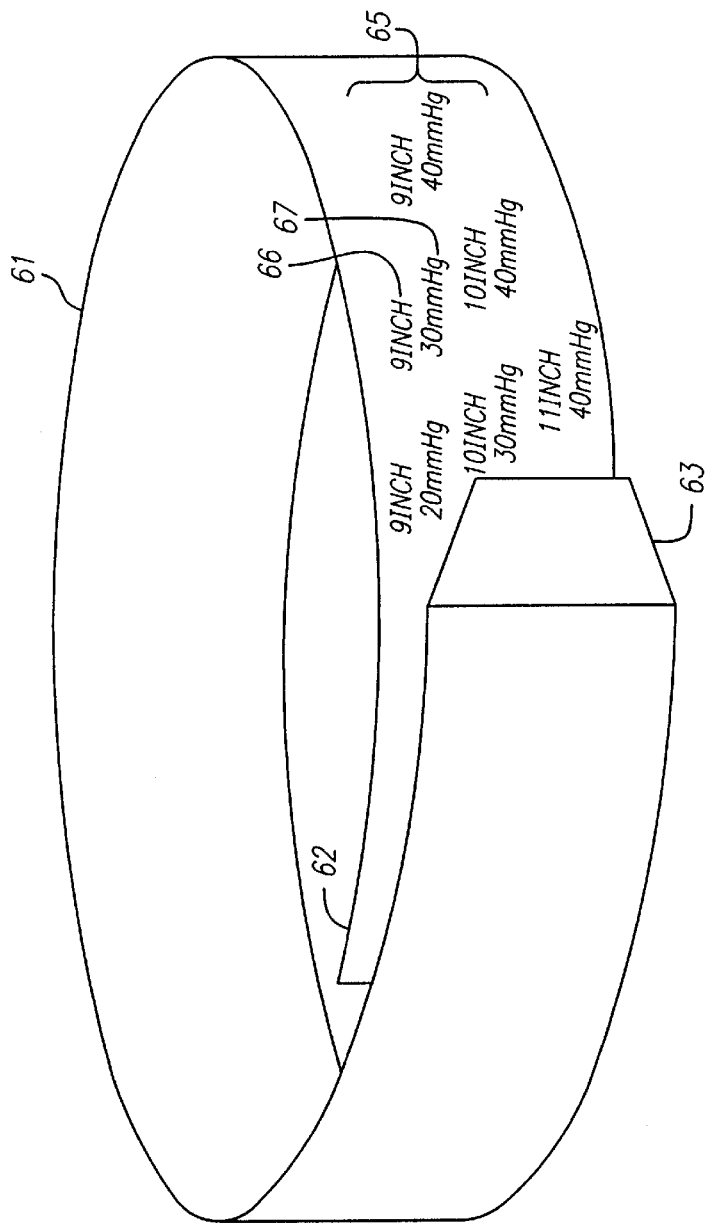

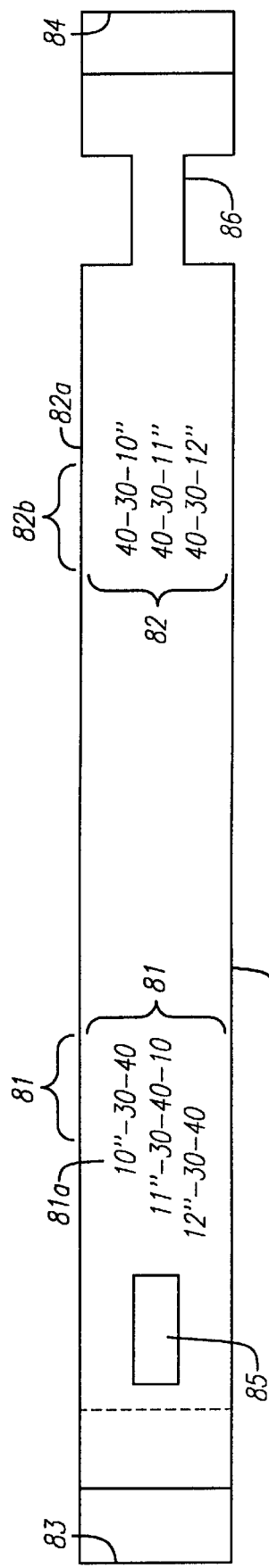
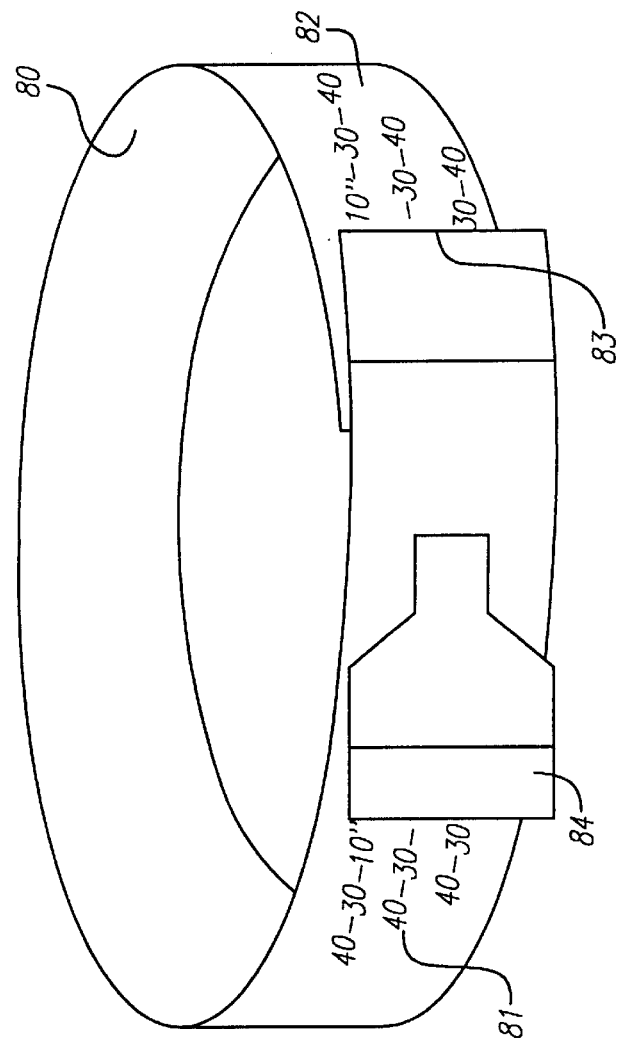
FIG. 27
FIG. 28

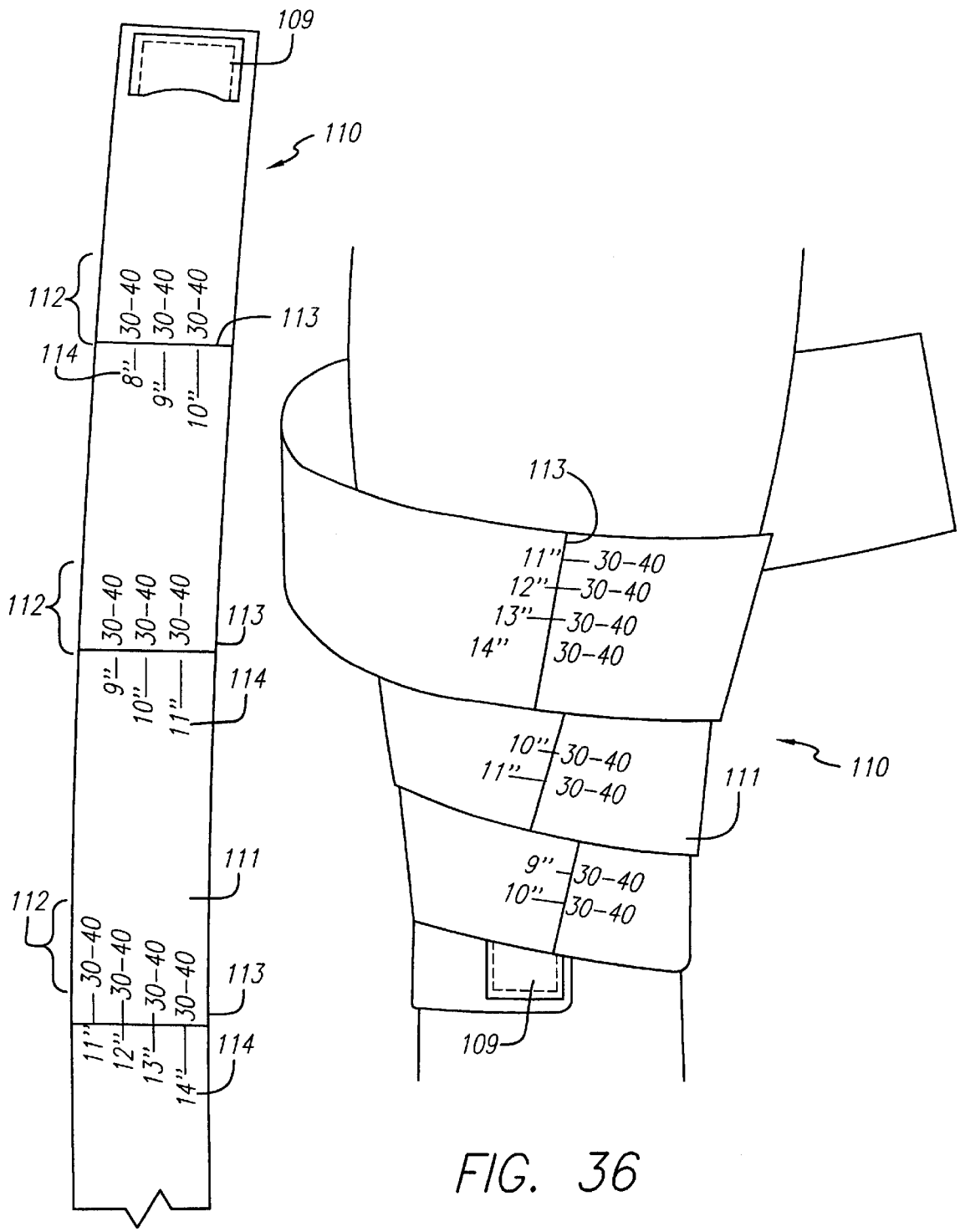

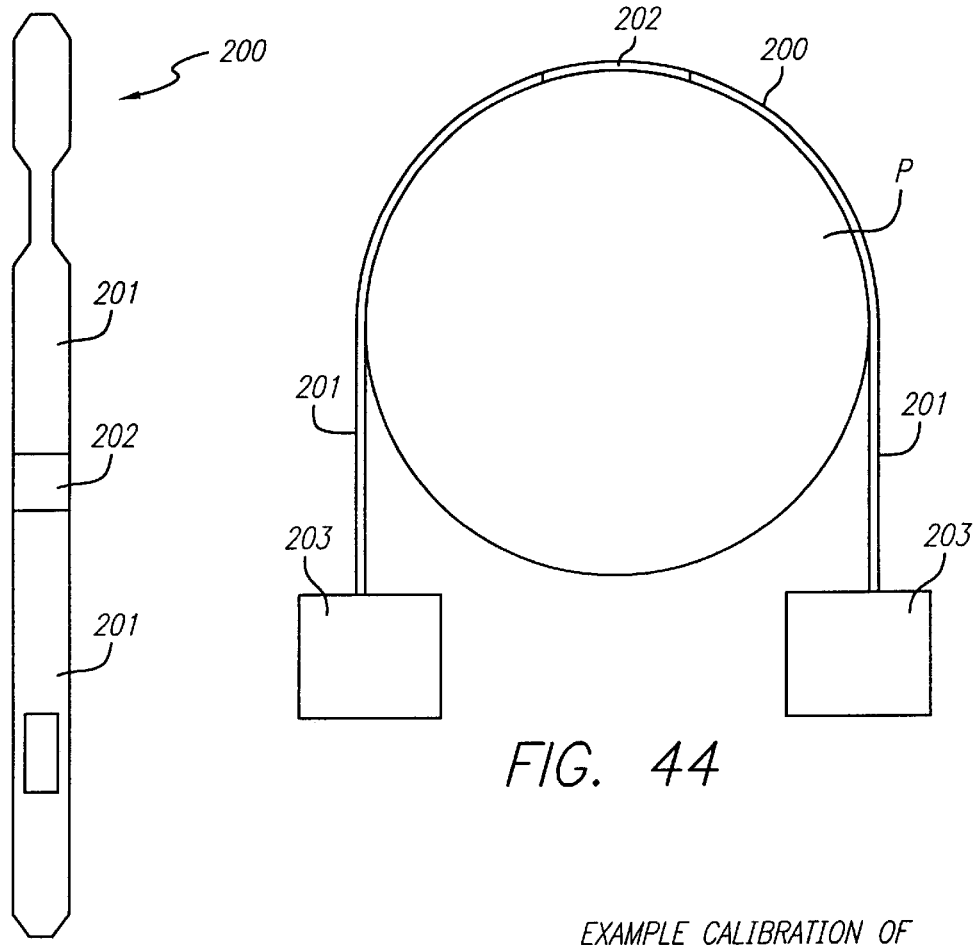
FIG. 43
FIG. 44
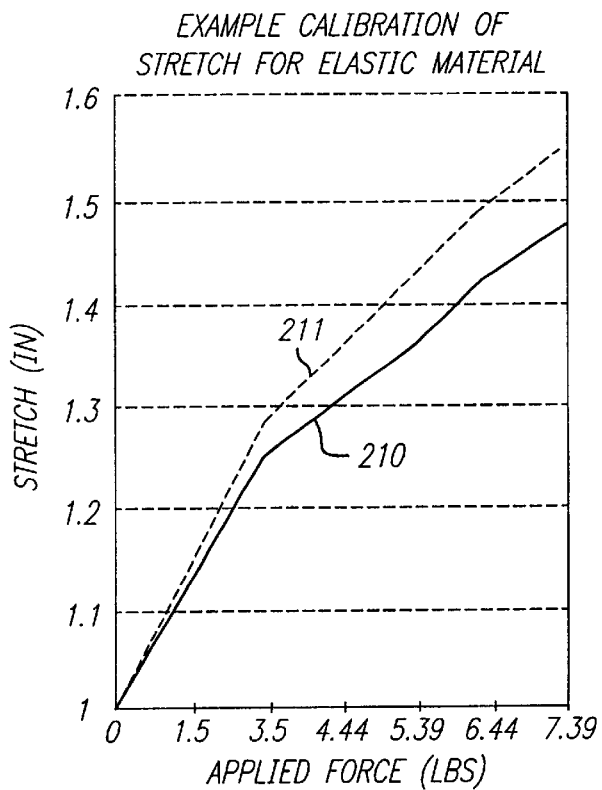
FIG. 45

COMPRESSION DEVICE WITH COMPRESSION MEASURING SYSTEM

CROSS-REFERENCE TO PROVISIONAL APPLICATION

This application is related to our now abandoned provisional application No. 60/100,511 filed on Sep. 16, 1998, the specification and drawings of which are specifically incorporated by reference.

BACKGROUND OF THE INVENTION

This invention relates to devices for applying compression to parts of the body for therapeutic reasons.

Compression applied to a body part, such as a limb, is essential for resolving many circulatory disorders. The application of compression at a required level has therapeutic benefits. For example, it restores circulation, relieves swelling, treats pain, heals ulcers, and heals varicose veins. Compression levels often must be adjusted quickly and easily in order to promote healing and prevent complications.

Circulatory disorders are chronic conditions for most patients with swelling of limbs. The application of compression to the limbs either during the day, overnight or both is necessary to relieve the swelling. Different levels of compression are necessary depending on the type and severity of the circulatory disorder and whether a person is lying down or standing up. A therapeutic goal is to apply the proper useful amount of pressure to a body part to maintain circulation. Furthermore, sustained compression at predetermined levels is the optimum therapy. (Callam, M. J. et al., Hazards of compression treatment of the leg: an estimate from Scottish surgeons, British Medical Journal 295(1987); Stemmer, R., Ambulatory elasto-compressive treatment of the lower extremities particularly with elastic stockings, Sonderdruck "Der Kassenartz" Mittellungsblatt des Deutschen Kassenarztverbandes (1969); Husni, E. A., "Elastic Support of the Lower Limb, Use and Abuse").

Elastic and non-elastic compression devices, such as elastic stockings, elastic cloth strip (e.g., "ACE" brand) wraps and bandaging systems, and non-elastic, adjustable garments all provide a range of compression, but none actually have an integral gauge or system whereby compression levels can be measured within a specified range as diurnal changes occur or as the patient changes posture. For example, the pressure required when lying down is less than the pressure required when the patient is ambulatory.

Commercially available elastic stockings with no ability for adjustment are made to various compression levels and sizes based on the circumference of the body part. Thus, a person may need several different stockings with varying compression levels depending on the nature and severity of the disorder and whether they are lying down or standing up. Elastic stockings are difficult to apply and remove, and lose compression over time. Elastic cloth strip wraps and bandaging systems are difficult to apply, have to be totally removed and re-applied to adjust compression levels, and do not indicate a compression level. Circulation can be cut off or other complications may occur if they are not applied properly.

One of the more pernicious dangers of elastic cloth strip wrap and bandaging systems is the possibility of unknowingly creating a reverse compression gradient. Thus, the elastic cloth strip inadvertently might be wrapped about the limb so as to apply more pressure at the proximal end of the limb than at the distal end, creating a "tourniquet effect" whereby fluids actually collect in the limb, causing further swelling.

Different diseases require different levels of compression, highlighting the need for a measurable and adjustable compression gradient. A burn victim or someone with both arterial and venous insufficiency may need the bare minimum therapeutic level of consistent compression (so that a therapeutic compromise is reached to allow optimal blood flow and fluid drainage) whereas a patient with lymphedema may require a higher level of consistent compression.

Patients have observed that stockings, wraps and bandaging systems made entirely of elastic materials are uncomfortable. Compression requirements change according to whether the patient is upright or prone. Fully elastic devices deliver an unchanging level of pressure, however, which alternately feels either "too tight" or "too loose" to the patient depending on the patient's position.

Indeed, most of the compression devices currently on the market suffer various other degrees of shortcomings, particularly in difficulty of application and removal, lack of adjustability, loss of compression, and discomfort.

Compression bandages are known that indicate the compression provided by the bandage. These compression bandages provide visual indications of varying amounts of elongation and thus tension. See U.S. Pat. No. 3,613,679 to Bijou for "Elastic Bandage with Tension Indicator" and U.S. Pat. No. 5,195,950 to Delannoy for "Compression Bandage with Calibration Means." These patents show compression bandages that have various geometrical forms or markings printed over the whole length of the bandages.

Seton Healthcare Group pic of Oldham, England has sold a "P.E.C. high compression bandage" under the trademark "SETOPRESS" for the treatment of varicose ulcers and associated conditions that has "visual guides" indelibly printed on both sides of an elastic bandage to ensure correct application resulting in either high or medium compression. These visual guides are colored rectangles, brown for "high" compression and green for "medium" compression. When the bandage is stretched the rectangles become squares. The brown rectangles are longer than the green rectangles crosswise or in the direction perpendicular to the longitudinal extension of the bandage. The bandage must be stretched more for the brown rectangles to become squares and therefore brown squares indicate a higher degree of tension in the bandage due to greater elongation. A table is provided in the accompanying instructions to correlate the extension of the bandage (as indicated by the rectangle/square visual guides), when the bandage is wound spirally with a 50% overlap, to the compression in the wrapped limb for different limb circumferences.

Another approach to providing predetermined compression to a limb that uses colored indicia is disclosed in Smith & Nephew's PLC's published international application number WO 97/39709 (international application no. PCT/GB97/01078) for a "Compression Device."

Patients and medical technicians should be able to accurately and reliably set a specific desired compression or compression gradient and be able to easily maintain and adjust the compression or compression gradient as necessary. None of the current devices have these properties.

Compression devices therefore are needed that have measuring systems for predicting and measuring the compression or compression gradient when users wear the devices. A need thus exists for a compression device with a system for measuring the compression provided by the device so that the device can be easily and rapidly adjusted to provide a correct and sustained compression or compression gradient and to quickly change the compression and compression gradient. A need also exists for compression devices with compression measurement systems that are easy to apply to and remove from parts of the body that have varying circumference and that are comfortable to wear throughout the day and in different postures.

Sustained compression is key to proper treatment. It is often a problem with compression devices that the applied compression goes down over time or with fluctuations in limb volume. The ability to measure compression and adjust easily enables compression to be maintained at an appropriate level.

SUMMARY OF THE INVENTION

The compression device according to the invention provides a band for applying compression to an object such as a part of the body, and a system for measuring the compression provided by the device so that a prescribed or desired compression can be easily applied to the body part and quickly adjusted as necessary for a therapeutic purpose such as to relieve swelling caused by a circulatory disorder or trauma. As used in this specification, "band" means any device that encircles or surrounds at least a portion of an object such as a body part and can include in its meaning a strap, wrap, sleeve or garment, or any combination of such devices.

The compression measuring, application, and adjustment system provided by the invention are based upon the known elastic or stretch properties of an elastic fabric or material comprising the device's bands, straps, wraps, sleeve or garment. The elastic component of the compression device will stretch when placed under tension. The measure of the stretch along an elastic axis of the elastic component is correlated to the tension along the elastic axis. The compression provided by the device is proportional to the tension when the elastic axis has a component parallel to the circumference of the body part or limb (that is, the elastic axis and thus the tension have components perpendicular to the longitudinal direction of the body part or limb). The compression is inversely proportional to the circumference of the body part. The system of the invention measures the stretch and provides the corresponding compression as a function of the previously measured circumference of the body part.

The system may be a combination of indicia printed at intervals on the device and a separate scale or measuring device such as a card for measuring the separation of the indicia and making the conversion of stretch to compression as a function of circumference.

In another embodiment of the invention, the system comprises scales printed on the device. The position of a free end of the device with respect to the scales varies with stretch and indicates the tension in the device and thus the compression for a given circumference. The scales in this embodiment may include markings for measuring the circumference of the body part so that the correct scale is chosen for reading the compression.

Pockets may be attached to the free ends of bands or sub-bands that are sized to permit the insertion of one or more fingers. This will allow the user to pull or push the free ends of the bands or sub-bands in order to tighten them and thus apply tension to a compression device so that it will provide the appropriate compression to the underlying body part.

OBJECTS OF THE INVENTION

An object of the present invention therefore is to provide compression devices with systems for allowing the user to accurately and reliably predict and measure compression levels.

Another object of the present invention therefore is to provide compression devices with systems for allowing the user to accurately and reliably apply pre-selected compression levels.

Yet another object of the present invention is to provide compression devices with systems for allowing the user to quickly change the compression levels being applied by the devices to new compression levels.

Another object of the present invention is to provide compression devices with systems that allow the user to accurately and conveniently change the compression levels being applied by the devices to the different compression levels required by different postures.

Still another object of the present invention is to provide compression devices with systems for allowing the user to quickly change the compression levels being applied by a device without having to remove the device from the body part or limb.

A further object of the present invention is to provide compression devices with systems for measuring compression so that a consistent tension will be present in all parts of the device in order to create an automatic distal-proximal compression gradient along the body part.

A still further object of the invention is to provide compression devices that are comfortable to wear.

Another object of the invention is to provide compression devices that are easily applied to and removed from parts of the body.

Yet another object of the invention is to provide compression devices that contain integral circumference measuring systems.

Still another object of the invention is to provide compression devices that are easy to tighten when setting the compression to be applied by the devices.

Yet another object of the invention is to provide compression devices that provide effective treatment.

DESCRIPTION OF THE DRAWINGS

Other objects, features, and advantages of the present invention will become more fully apparent from the following detailed description of preferred embodiments, the appended claims, and the accompanying drawings in which:

FIG. 22 is a view of another preferred embodiment of the compression device according to our invention.

FIG. 23 is another view of the compression device shown in FIG. 22.

FIG. 27 is a view of a variation of the compression device shown in FIG. 24.

FIG. 28 is another view of the compression device shown in FIG. 27.

FIG. 35 is a side view of another embodiment of the compression device according to our invention.

FIG. 36 is a perspective view of the compression device shown in FIG. 35, being placed on the lower leg of a person.

FIG. 43 is a view of a band used to empirically calibrate the stretch of an elastic material a function of force.

FIG. 44 is a simplified view of an apparatus for empirically measuring stretch of an elastic material as a function of force.

FIG. 45 is a graph showing the stretch of an elastic material as a function of force with and without friction.

Figure 1:
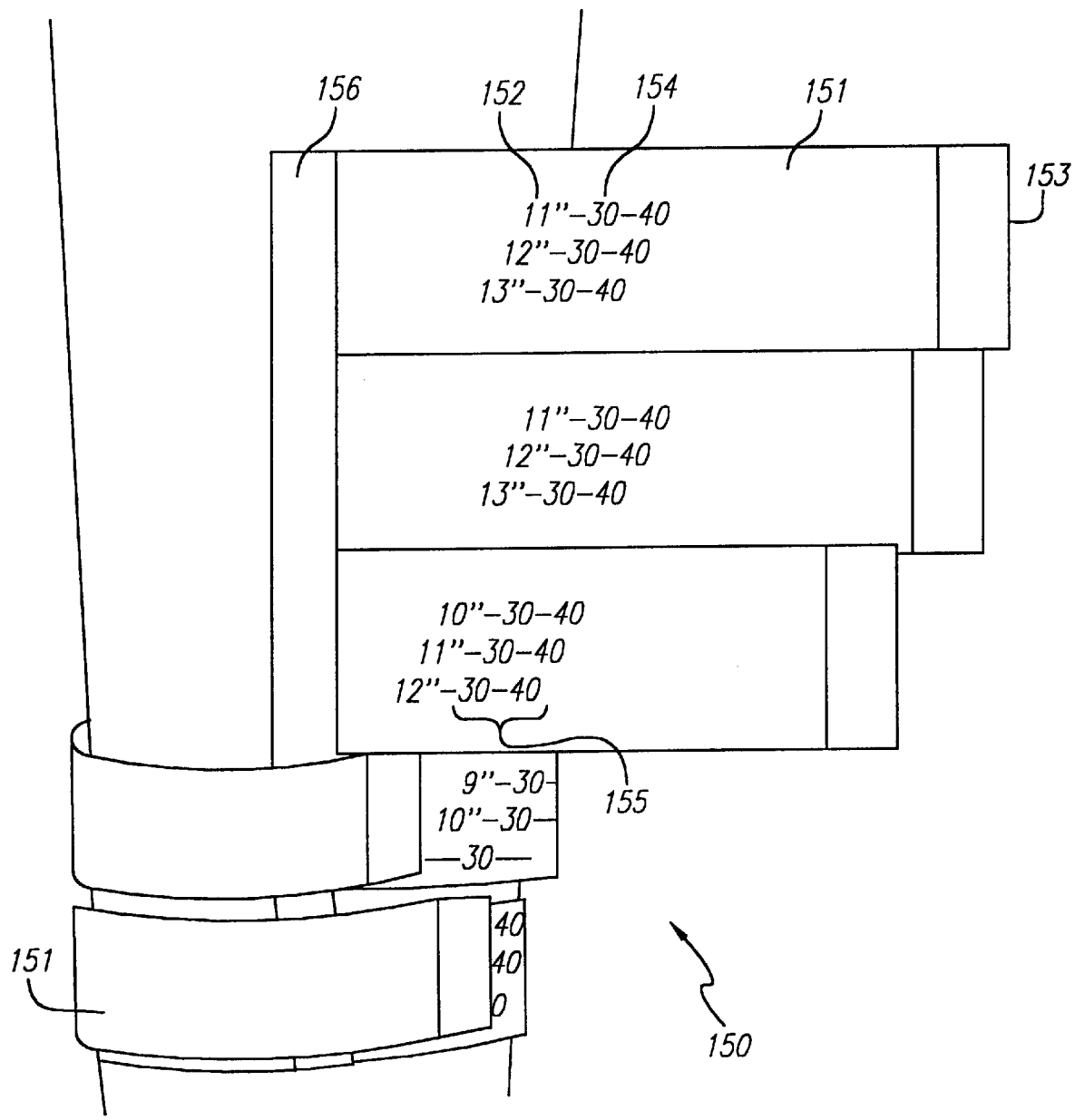
FIG. 1 is a side perspective view of a preferred embodiment of the compression device according to our invention shown attached to the leg of a human being.

REFERENCE NUMERALS IN THE DRAWINGS 1a compression device
1b compression device
1c compression device
2 band
3 interval
4 indicia
4a indicia
5 anchor
6 fastener
L Leg
F Foot
7a card
7b card
7c card
8a edge
8b edge
8c edge
9a measurement scale
9b measurement scale
9c measurement scale
10a face
10b face
10cc face
11 reference mark
12a measurement marks
12b measurement marks
12c measurement marks
13 band
14 band
15 central region
16 fastener
20 compression device
20a compression device
20b compression device
20c compression device
20d compression device
20e compression device
21 sheet
21a sheet
22 end of sheet
23 elastic band
23a elastic band
24 sleeve
25 indicia line
25a indicia line
26 slit
26a slit 27 sub-band
27a sub-band
27b fold
28 fastener
28a fastener
28b direction of pulling fastener
29 padding
30 hand band
31 distal end of sleeve
32 free end of hand band
33 fastener
34 dart
35 edge
36 edge
37 edge
37a edge
38 edge
38a edge
39 edge
40 edge
41 sheet
41a sheet
42 elastic band portion
42a elastic band portion length
42b elastic band portion width
43 sub-band
43a sub-band
43b sub-band
43c sub-band
43d sub-band
43e sub-band
44 slit
44a slit
45 slot
46 neck
47 hole
48 hook surface fastener
48a hook surface fastener
50 D-ring
51 base end
52 inelastic band
53 elastic band
54 free end
55 fastener
56 female member
57 male member
58 slot
59 neck
60 indicia line
61 compression device
62 base end
63 free end
64 fastener
65 compression measurement indicia
66 circumference marking
67 compression markings
70 band
71 base end
72 free end
73 fastener
74 scale
75 circumference marking
76 compression marks
80 band
81 scale set
81a circumference marking
81b compression marks
82 scale set
82a circumference marking
82b compression marks
83 end
84 end
85 slot
86 neck
90 band
90a band
91 end
92 end
93 D-ring
94 set of scales
94a set of scales
94b set of scales
95 band
96 end
97 end
98 set of scales
99 set of scales
100 band
101 pocket
102 end
103 pocket edge
104 open pocket edge
105 space
106 end
107 fastener
108 outside surface
109 pocket
110 compression device
110a compression device
111 band
111a band
112 set of scales
112a set of scales
113 reference marker
113a reference marker
114 circumference marking
114a circumference marking
115 spacing
120 compression device
121 elastic band
121a elastic band
121b elastic band
121c elastic band
122 indicia lines
122a indicia lines
122b indicia lines
122c indicia lines
123 sub-band
123a male sub-band
123b female sub-band
130 compression device
131 sheet
132 band portion
133 parallel lines
134 sub-bands
135 pocket
135a sub-pocket
136 fasteners
150 compression device
151 band
152 circumference marker
153 free end
154 compression mark
155 scale 156 strip
200 calibration test band
201 inelastic component
202 elastic component
P model body part
203 weights
210 plot of stretch as a function of force (with friction)
211 plot of stretch as a function of force (without friction)

DETAILED DESCRIPTION OF THE
PREFERRED EMBODIMENTS

Figure 2:
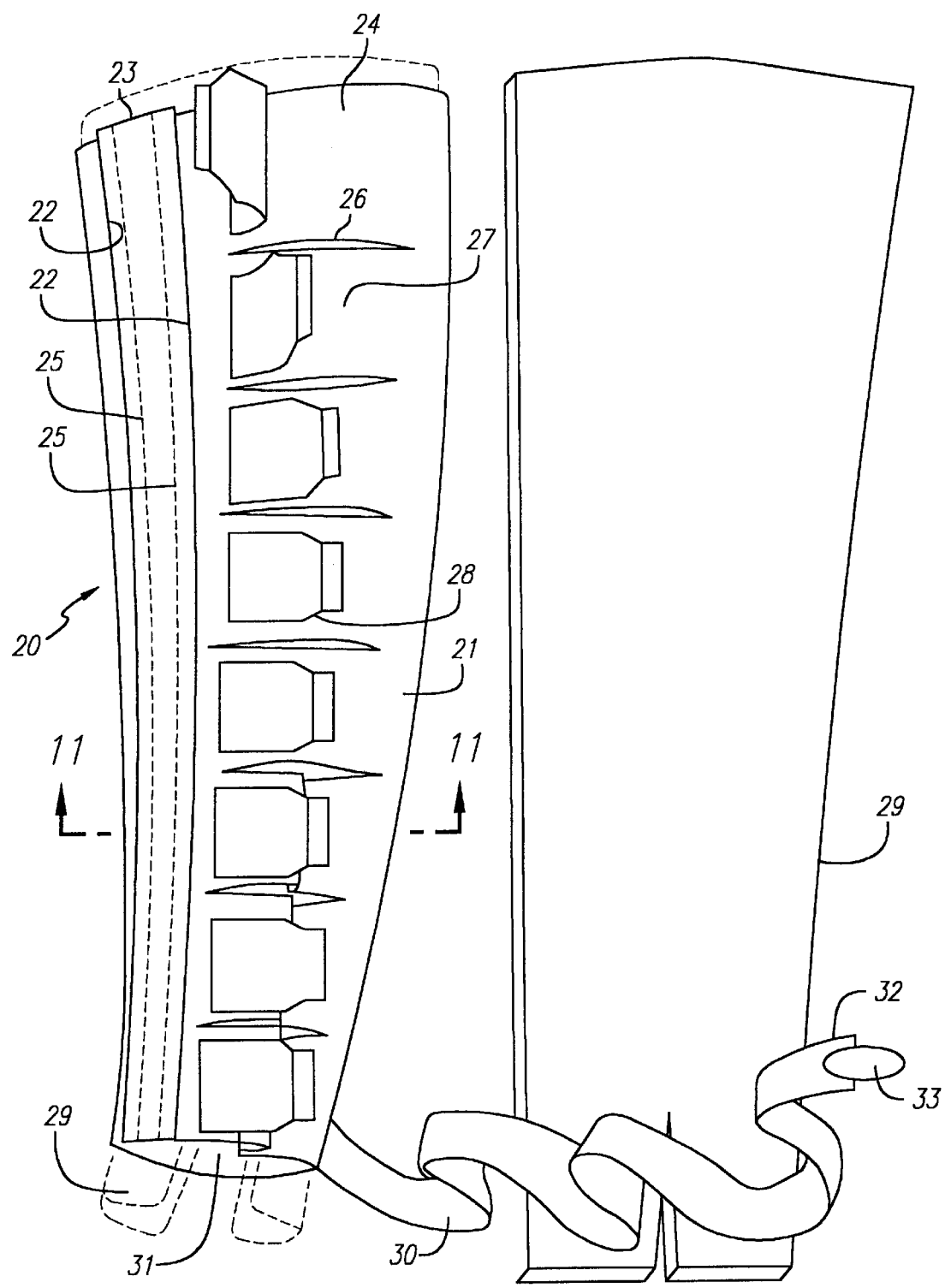
FIG. 2 is a side perspective view of another preferred embodiment of the compression device according to our invention for attachment to the arm of a human being.

FIGS. 1 and 2 show the currently most preferred embodiments of the compression device with compression measuring system according to our invention. In FIG. 1 the compression measuring system is completely integral to the compression device, i.e., no other equipment is needed to measure and apply the compression provided by the compression device. The compression device of FIG. 2, however, requires a separate measuring unit in the form of a card. These particular embodiments, which are discussed in greater detail in later parts of the specification, exemplify two principal means for providing compression devices with compression measuring systems.

One preferred embodiment of the compression device according to the invention provides one or more bands that are wrapped around a body part or other material (FIGS. 3–6) and a calibrated measuring scale or card (FIGS. 7–9) that is used in combination with the bands to measure the stretch of elastic in the bands.

Figure 3:
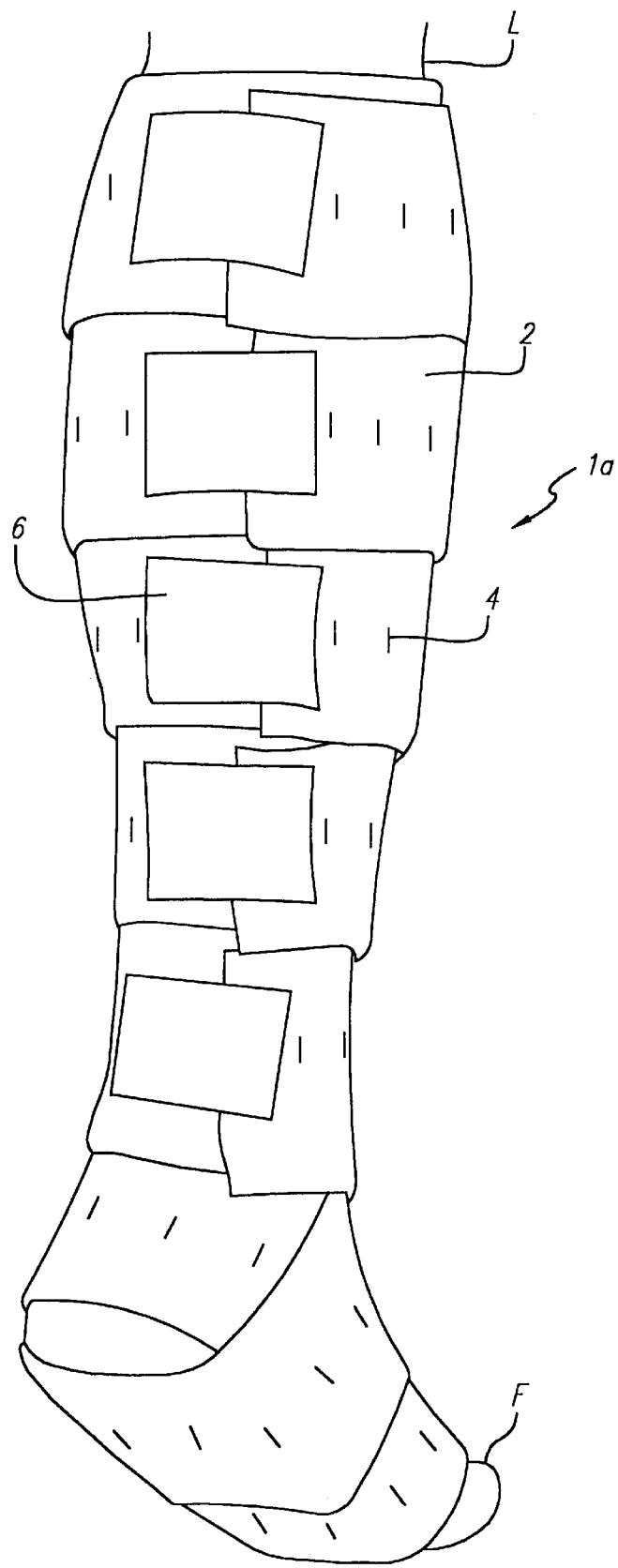
FIG. 3 is a side perspective view of another preferred embodiment of the compression device according to our invention shown attached to the leg of a human being.
Figure 4:
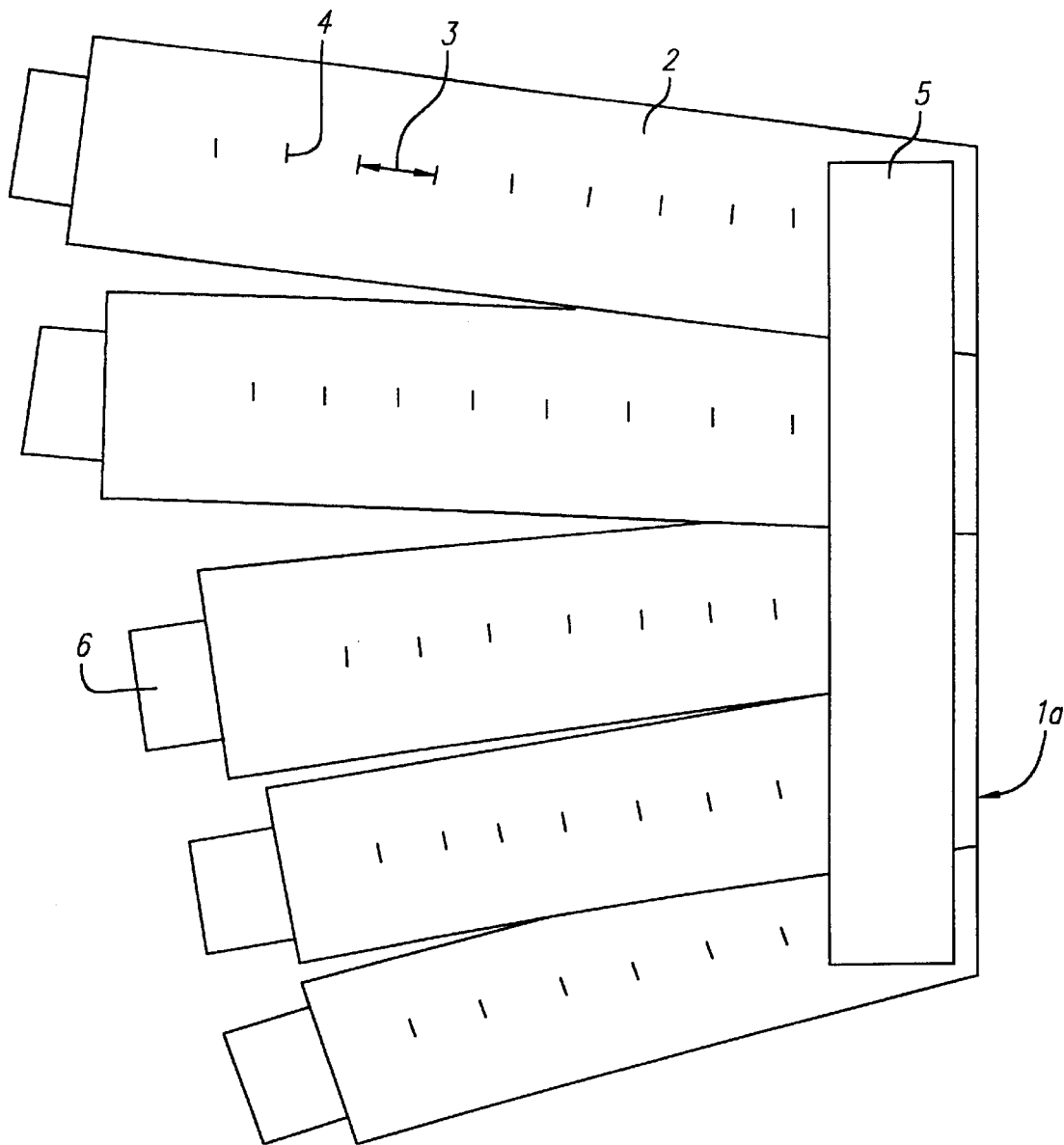
FIG. 4 is a view of the compression device shown in FIG. 3 when not attached to the leg of a human being and unfurled.

FIGS. 3 and 4 show a compression device 1a consisting of several bands 2. The compression device 1a shown in FIG. 3 is intended to be applied to or wrapped around a part of a human body, in this case the lower part of a leg L and a foot F. The compression device 1a is shown in FIG. 4 in an unfurled and untensioned condition in which it is unattached to a part of the body.

Figure 5:
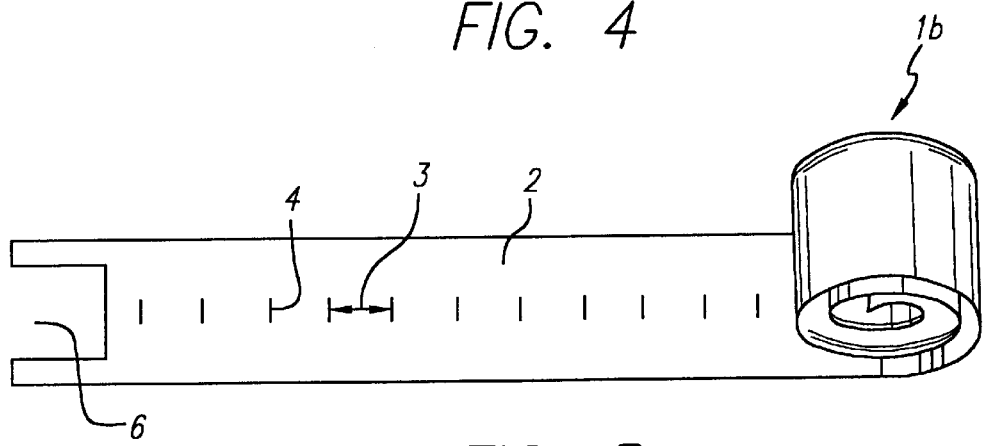
FIG. 5 is a perspective view of another preferred embodiment of the compression device according to our invention.

FIG. 5 shows a variant compression device 1b consisting of a single one of the bands 2.

Each band 2 is elastic or substantially elastic along its length or longitudinal axis. It is therefore elastic or substantially elastic along an axis referred to in this specification as the elastic axis, which is the axis along which tension is to be applied. Each band 2 could be made, of course, so that it is elastic along only a part of its length. The elastic axis of the bands 2 of FIGS. 3–5 is the lengthwise axis of the bands 2, not the width of the bands 2. Each band 2 has indicia 4 printed along its elastic length, or elastic axis, spaced by intervals 3. The interval 3 has a fixed or specified length when the band is not under tension, as in FIGS. 4 and 5.

The bands 2 are made of a loop fabric or material (such as that sold under the trademark VELCRO) so that hook material (such as that also sold under the trademark VELCRO) will attach to the bands 2.

The length of the different bands 2 in the device 1a can vary to accommodate body parts, such as the leg L and the foot F, that vary in circumference over their lengths. The bands 2 are joined to each other at one of their ends using an anchor 5 made of a strip of hook material. The anchor 5 runs roughly perpendicular to the bands 2, and functions to stiffen the device 1a and hold the bands 2 in place on the body parts L and F. The anchor 5 also could be sewn (or attached by other means known to those of skill in the art) to the bands 2, in which case it need not be made of hook material.

Fasteners 6, made of shorter pieces of hook material, are attached to the unanchored ends of the individual bands 2 for attachment purposes. Each of the bands 2 is pulled under tension around one of the body parts L and F to enclose a portion of that body part, and attached to itself using a fastener 6, thus applying compression to that portion of the body part (as shown in FIG. 3).

Figure 6:
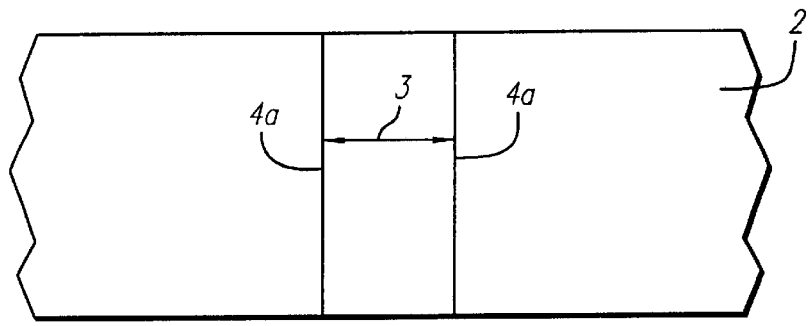
FIG. 6 is a view of a portion of another preferred embodiment of the compression device according to our invention.

In the compression device 1a shown in FIGS. 3–4, the indicia are two or more tick marks 4 spaced along the width of the band at intervals 3. Other embodiments of the indicia 4 could include dots, geometric shapes, symbols, patterns, text, or any other pattern spaced at intervals 3 along the elastic axis of the band 2 for measurement with a calibrated scale or card (as discussed below) upon application of the band or bands 2 to the body part and stretching of the band or bands 2. The intervals 3 are preferably at a uniform or specified distance from each other when the bands 2 are relaxed and not under tension, as shown in FIGS. 4 and 5. In FIG. 6 a portion of a band 2 is shown in which the indicia 4a are two or more parallel lines spanning the width of the elastic band 2 and spaced at intervals 3.

The measurement of elastic stretch or deformation along the elastic axis (depending upon the specific form of the embodiment), upon application of the device 1A or 1B to the body part, serves to accurately measure compression of the underlying body part. The interval 3 between successive indicia 4 will increase when the band 2 is tensioned and the elastic material of the band lengthens under tension. The user measures the distance between successive ones of the indicia 4 after application of the device 1a or 1b to the body part. This distance is indicative of the tension in the elastic material of the band 2 and, when the circumference of the body part is known, the compression applied by the device 1a or 1b.

FIG. 5 shows an embodiment of the device 1b having one long band 2 with indicia 4 in the form of tick marks printed along its length or elastic axis. A fastener 6 made of hook material is attached to the ends of the band 2. The band 2 is wrapped around a body part, and the two ends are held in place using the fastener 6. After the user measures the circumference of the body part, a scale or card is used to determine the compression of the body part. As described below, the card is used to establish or verify equal or varying tension at different positions of the band as necessary. As an example, the natural distal-to-proximal increase of circumference of a body part such as a limb automatically yields a gradient of compression running up the limb for equal measured tension, without the user having to set a different target compression for different positions on the limb. The band 2 is removed or adjusted by lifting the fastener 6 from the band 2, and unwrapping or re-wrapping the band 2.

The compression devices 1a or 1b require the use of means for measuring the distance between the indicia 4 or 4a on a band 2 and means for correlating that distance to the amount of tension and/or, if the circumference of the body part is known, to the amount of compression of the body part surrounded by the band 2. A card (reference numerals 7a–7c) having a plurality of edges (8a–8c) with measurement scales (9a–9c) is currently preferred to accomplish this function with respect to the compression devices 1 or 1a (see FIGS. 7–9) and other embodiments to be discussed later in this specification.

The card (7a–7c) will indicate the compression applied by the band 2 for different circumferences of the body part. The card (7a–7c) therefore preferably will have at least one edge (8a–8c) for each compression level or, alternatively, size range of circumferences of the body part that might be desirable. The card (7a–7c) contains measurement scales (9a–9c) for use in measuring the interval 3 between successive indicia 4 on the bands 2. The measurement scales (9a–9c) are labeled to indicate the compression achieved for particular intervals 3 and circumferences of the body part.

The card (7a–7c) is made from plastic, cardboard, or another sheet material and has two sides or faces (10a–10c). The card (7a–7c) is a polygon or other shape with at least three edges. The measurement scales (9a–9c) are printed on one or more of the edges (8a–8c) of the card (7a–7c), on one or both faces (10a–10c) of the card (7a–7c), and each scale (9a–9c) has several marks. These measurement scales (9a–9c) are calibrated to measure the distance between the indicia on the elastic material used in the bands 2 after the bands 2 are applied to the body part and the intervals 3 between successive indicia 4 change. The calibration of the scales can also be set to account for multiple layers of fabric, or angles in the wrapping of the bands 2.

The "sizes" of circumference preferably correspond to ranges of circumferences. Exemplary preferred ranges of circumference are identified in the table below.

| Size | Range of Circumference (inches) |
|---|---|
| XSMALL | 4–6 |
| SMALL | 6–8 |
| MEDIUM | 8–10 |
| LARGE | 10–13 |
| XLARGE | 13–16 |

Devices for different body parts or that incorporate different amounts of padding would require different ranges.

The circumference may be that of the body part itself or that of the compression device when placed around the body part, as long as the method of measuring the circumference is consistent and the conversion or calibration to compression accounts for the method of measuring the circumference.

One way of calibrating the scales to account for multiple layers of fabric or angles in the wrapping of the band or bands 2 is to use a conversion chart. For example, when wrapping the ankle and foot with a band 2, such as that shown in FIG. 5, two measurements may be taken of the circumference of the foot (at the arch and at the ankle bone). These measurements are used with a table to select a corrected size or range of circumference, which is then used in making the measurement with the card 7a–7c. The corrected size takes into account the additional measurement required for the foot, plus accounting for angling and layering of the band 2. An example of a conversion chart is reproduced below.

| | | Circumference at ankle bone (inches) | | | | | |
|---|---|---|---|---|---|---|---|
| | | 6–8 | 8–10 | 10–12 | 14–16 | 16–18 | 18–20 |
| Circumference at middle of arch of foot (inches) | 6–8 | Xsmall | Xsmall | Xsmall | Small | Small | Small |
| | 8–10 | Xsmall | Xsmall | Small | Small | Small | Med |
| | 10–12 | Xsmall | Small | Small | Small | Med | Med |
| | 12–14 | Small | Small | Small | Med | Med | Med |

The card (7a–7c) is used to set the compression applied by the band 2 to the foot and ankle in view of the corrected size.

Figure 7:
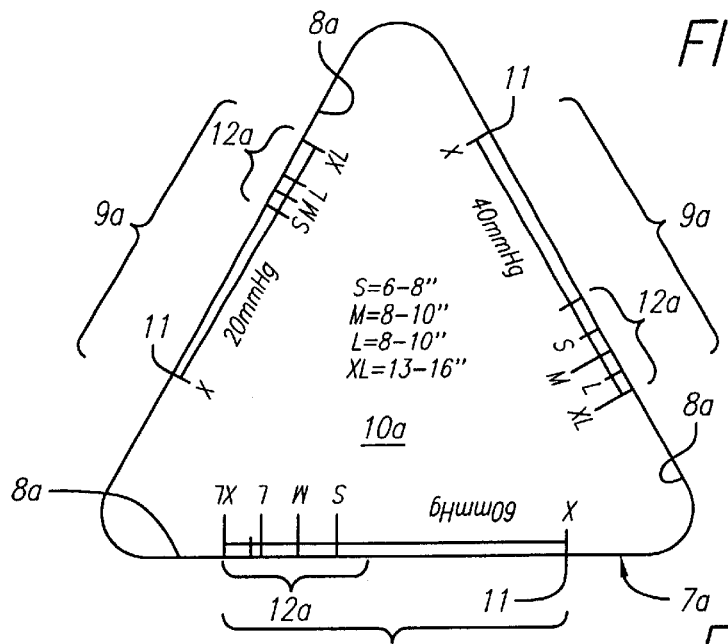
FIG. 7 is a view of a card for measuring and setting the compression provided by a compression device according to our invention.
Figure 8:
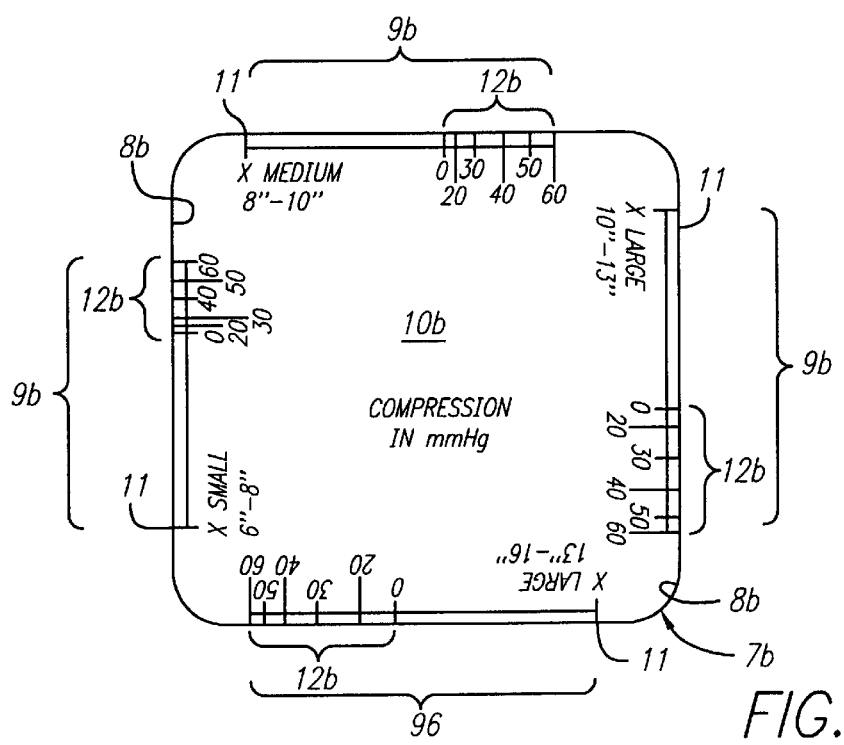
FIG. 8 is a view of another card for measuring and setting the compression provided by a compression device according to our invention.
Figure 9:
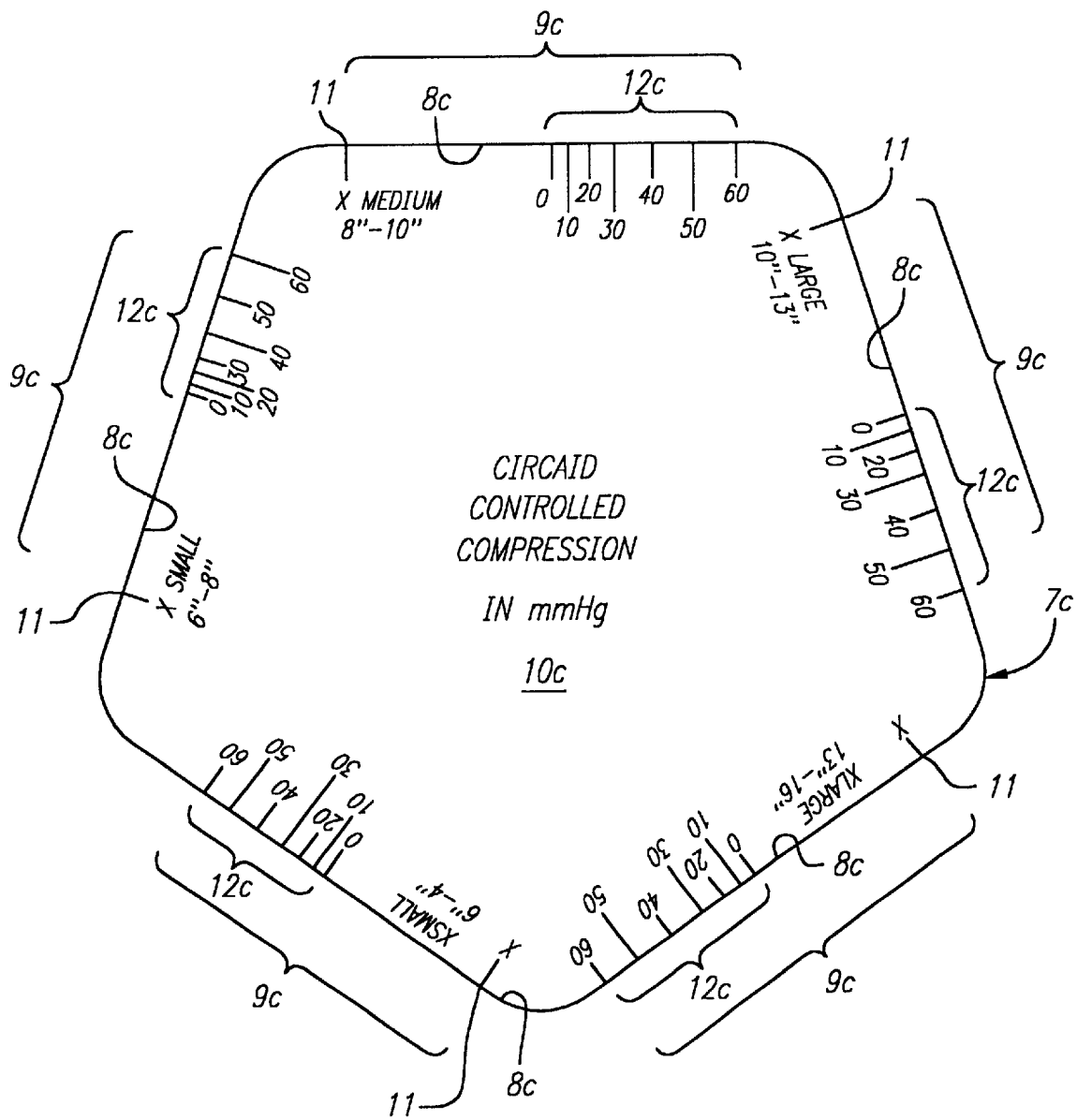
FIG. 9 is a view of another card for measuring and setting the compression provided by a compression device according to our invention.

In the embodiments shown in FIGS. 7–9, the different measurement scales (9a–9c) correlate the different sizes/circumferences of the body part to the target compression to be applied. In the embodiment shown in FIG. 7, the card 7a is triangular, with measurement scales 9a printed on the three edges 8a of at least one face 10a of the card 7a, one for each of three target compression levels. Each measurement scale 9a on the card 7a shown in FIG. 7 has a reference mark 11 and measurement marks 12a corresponding to different limb circumference size ranges. The measurement marks 12a have different spacings and locations on each of the measurement scales 9a because a different tension and thus stretch, as measured by the separation between intervals 3, will be necessary to achieve the compression of a particular scale 9a for different circumferences of the body part.

In the embodiment of the card 7b shown in FIG. 8, the card 7b is square with four edges 8b each having a measurement scale 9b. Each of the measurement scales 9b corresponds to a different limb size range. Each measurement scale 9b of the card 7b shown in FIG. 8 has a reference mark 11 and measurement marks 12b corresponding to compression levels ranging from 0 mmHg to 60 mmHg. The measurement marks 12b have different spacings and locations on each of the measurement scales 9b because different intervals 3 and thus tensions will be necessary to achieve the various compressions for a given range of circumference of the body part.

Other units, of course, could be used to measure compression. Different compression levels could, of course, be assigned entirely arbitrary designations such as A, B, and C or colors such as green, red, and blue. The physician or other therapist prescribing a compression level could determine from experience the compression level corresponding to an arbitrary designation that is suitable for a particular patient. The compression measurement card would then be used, by selecting the arbitrary designation (e.g., red), to apply the desired compression level and keep it consistent along the body part in order to maintain a pressure gradient.

The card 7c shown in FIG. 9 is similar to that shown in FIG. 8, but has five rather than four edges. In this embodiment the card 7c is pentagonal with five edges 8c each having a measurement scale 9c. Each of the measurement scales 9c corresponds to a different limb size range. Each measurement scale 9c of the card of FIG. 9 has a reference mark 11 and measurement marks 12c corresponding to compression levels ranging from 0 mmHg to 60 mmHg. The measurement marks 12c have different spacings and locations on each of the measurement scales 9c because different intervals 3 and thus different tensions will be necessary to achieve the various compressions for a given range of circumference of the body part.

In use, the band or bands 2 are applied directly around a body part or around other material that surrounds a body part. Tension on the bands 2 causes the elastic to stretch, increasing the intervals 3 between successive indicia 4. If the circumference of the body part under the bands 2 is known, measuring the interval 3 of the indicia 4 provides a measure of compression under the bands 2.

The circumference of the body part can be measured using a soft measuring tape, and in systems of multiple bands a measurement can be taken at the position of each band. A compression measurement for each band 2 is achieved by holding an edge 8a–8c of the card 7a–7c having a measurement scale 9a–9c against the band 2, aligning the reference mark 11 of the measurement scale 9a–9c with one of the indicia, and observing where an adjacent indicia lines up with the measurement marks 12a–12c.

In the case of the card 7a show n in FIG. 7, after measuring circumference, the user would select the edge 8a of the card 7a corresponding to the correct compression, and would then use that edge 8a (and its related measurement scale 9a) of the card 7a to measure whether the interval 3 between the indicia 4 corresponds to the circumference range of the body part or limb.

In the case of the card 7b or 7c shown in FIGS. 8–9, the user, after measuring the circumference of the body part, would select the edge 8b or 8c of the card 7b or 7c having the measurement scale 9b or 9c for that circumference, and would then use that edge 8b or 8c of the card to read the compression from the interval 3 of the indicia 4.

If the circumference of the body part at the band 2 is known, the card 7b or 7c can be used to measure the compression of the body part. The band 2c an be adjusted to obtain the desired compression, by lifting up the fastener 6, adjusting the tension on the band 2, then reattaching the band 2 and using the card 7b or 7c to re-read the compression. The card 7a can be used to determine whether the compression has reached the compression of one of the measurement scales 9a and can thus also be used to measure and readjust the compression, although less directly.

The card 7b or 7c can be used to establish or verify equal or varying tension on each of the bands as necessary. As an example, the natural distal-to-proximal increase of circumference will automatically yield a gradient of compression running up the limb if the compression device 1a or 1b has equal tension throughout, without the user having to set a different target compression for each band 2 or winding of band 2. The band or bands 2 are removed or adjusted by lifting the fastener or fasteners 6 up from the band or bands 2, and unwrapping or re-wrapping the band or bands 2, reattaching the fastener 6 to the band or bands 2 to thereby adjust the tension. The tension is generally proportional to the size of the interval 3. If the card 7a–7c is used with this readjustment procedure to establish equally sized intervals 3 throughout the device 1a or 1b, then a greater net compression will be applied to the thinner part of the limb (the distal end) than the wider part of the limb (the proximal end).

Figure 10:
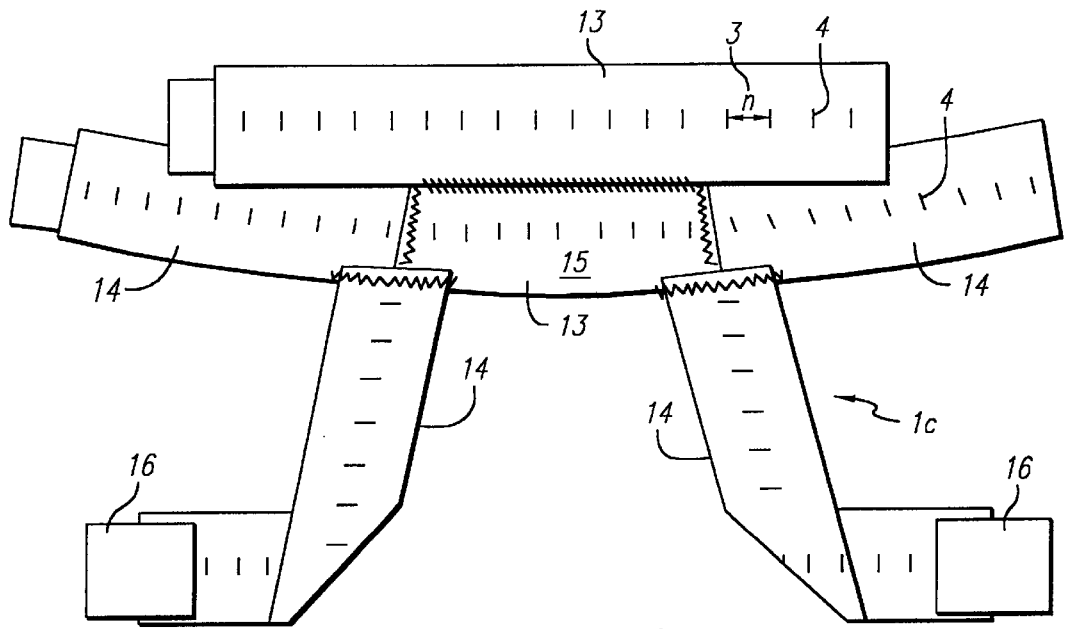
FIG. 10 is a view of another preferred embodiment of the compression device according to our invention.

FIG. 10 shows an embodiment 1c of the device that is an ankle-foot wrap assembled from elastic loop material bands 13 and 14 on which are printed indicia 4 in the form of tick marks running along the elastic axis of the bands 13 and 14, which in this embodiment is the length of the bands 13 and 14. The bands 13 are stitched together (or otherwise assembled) in such a way as to form a central region 15, with bands 14 stitched or otherwise attached to the central region 15. In use, the bands 13 and 14 are wrapped around the foot or ankle to apply compression, and hook material fasteners 16 are used to attach the ends of the bands 13 and 14. The card 7a–7c can be used to establish or verify equal or varying compression (or tension) on the bands 13 and 14 as necessary. The bands 13 and 14 can be removed or adjusted by lifting the fasteners 16 up from the bands 13 and 14, and unwrapping or re-wrapping the bands 13 or 14.

FIG. 2 shows an embodiment of a compression device according to the invention, indicated by reference numeral 20. A sheet 21 has two ends 22 each connected to a band 23, so as to form a sleeve 24. The sheet 21 is composed of substantially inelastic loop material, preferably VELCRO knit loop fabric 3800. The fabric is oriented in the device so that the greater stretch is in the longitudinal or vertical direction of the device and the lesser stretch is in the transverse or horizontal direction of the garment.

At least a portion of the band 23 is elastic along the entire width of the band 23 (i.e., in a direction perpendicular to the elastic axis), with the direction of stretch (the elastic axis) being parallel to the circumference of the sleeve 24. The band 23 may be elastic in other directions as well.

A preferred material for the band 23 is neoprene sheeting. The neoprene is preferably pure neoprene, such as that available from Perfectex Plus, Inc. of Huntington Beach, Calif., because of its more enduring elasticity. The thickness should be in a range such that a significant change in stretch is observed for a change in tension throughout the range of tensions to be used. A VELCRO-type loop material also may be laminated on the surface of the neoprene to protect the neoprene and improve the comfort of wear.

Two or more spaced indicia lines 25 are printed on the elastic part of the band 23 of the device 20, running along at least a portion of the width of the band 23, and serve as indicia to be used with the card 7a–7c (FIGS. 7–9) for determining compression as described above in connection with the devices 1a–1c. (One or more of the indicia lines also could be printed on the sheet 21 as long as a portion of the elastic band 23 separates the indicia lines 23.) The lines 25 preferably are parallel when the band 23 is not under tension, such as when the device 20 is not applied to a part of the body such as a limb.

One or more slits 26 are formed in the sheet 21, parallel to the circumference and running partially around the sleeve 24. These slits serve to separate the sleeve 24 into a series of sub-bands 27 (they are referred to as sub-bands because the entire sleeve is essentially one band). Onto each sub-band can be sewn or otherwise attached a fastener 28 preferably made at least in part of a piece of hook material or tape. Those of skill in the art will understand that other kinds of fasteners might be employed in place of hook material or tape.

The body part is slid into the sleeve 24, and, the sub-bands 27 can be tightened by lifting up the fasteners 28, pulling them around the limb, and then attaching them to the loop surface of the sheet 21, thus applying compression to the body part. As the sub-bands 27 are tightened around the limb, the card 7a–7c is held against the indicia 25. The card 7a–7c is used to measure the distance between the indicia 25 in the elastic axis of the band 23. Accordingly, the distance between the indicia 25 as measured by the card 7a–7c indicates what compression level has been obtained under the portion of the sleeve 24 associated with the adjacent sub-band 27, provided the circumference of the body part is known.

The sub-bands 27 can be adjusted to obtain the desired compression, by lifting up the fasteners 28, adjusting the tension on the sub-bands 27, then reattaching the fastener 28 and using the card 7a–7c to re-read the compression.

The card 7a–7c can be used to establish or verify equal or varying tension on the sub-bands 27 as necessary. As an example, the natural distal-to-proximal increase of circumference will automatically yield a gradient of compression running up the limb if there is equal tension (i.e., if the indicia lines 25 are parallel), without the user having to set a different target compression for each sub-band 27.

The sleeve 24 is removed by lifting the fasteners 28 off the loop material of the sheet 21, letting the sub-bands 27 relax to their full circumference, and sliding the sleeve 24 off of the body part.

Padding 29, made of foam or other resilient material, may be placed inside or attached to the inside of the sleeve 24, in order to provide protection to the limb and equally distribute compression from the sub-bands 27. In any embodiment of a compression device according to the present invention padding can be used to fill crevices or other irregularities in the body part as necessary, to ensure even tension and compression.

An elastic band 30 is attached to the distal end 31 of the sleeve 24, to be used to wrap around and thereby compress the hand or foot. The band 30 is preferably made of a loop material so that the free end 32 of the band 30 can be attached to another part of the band 30 (or to the sheet 21) using a fastener 33 made of a hook material.

Figure 11:
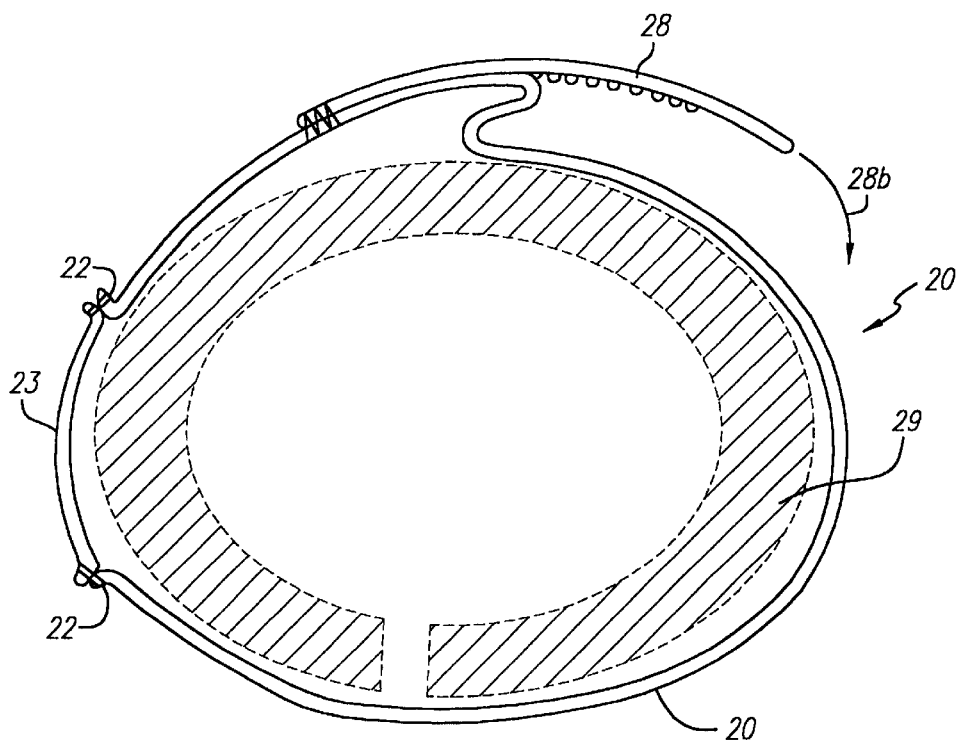
FIG. 11 is a cross-sectional view of the compression device shown in FIG. 2 taken along the line 11—11 of FIG. 2 in the direction of the arrows.

FIG. 11 is a cross-section view of the compression device 20 showing how the hook tape fastener 28 may be pulled around the limb, in the direction indicated by arrow 28b, and attached to the loop surface of the sheet 21, thus applying compression to the body part. Padding 29 protects the limb.

Figure 12:
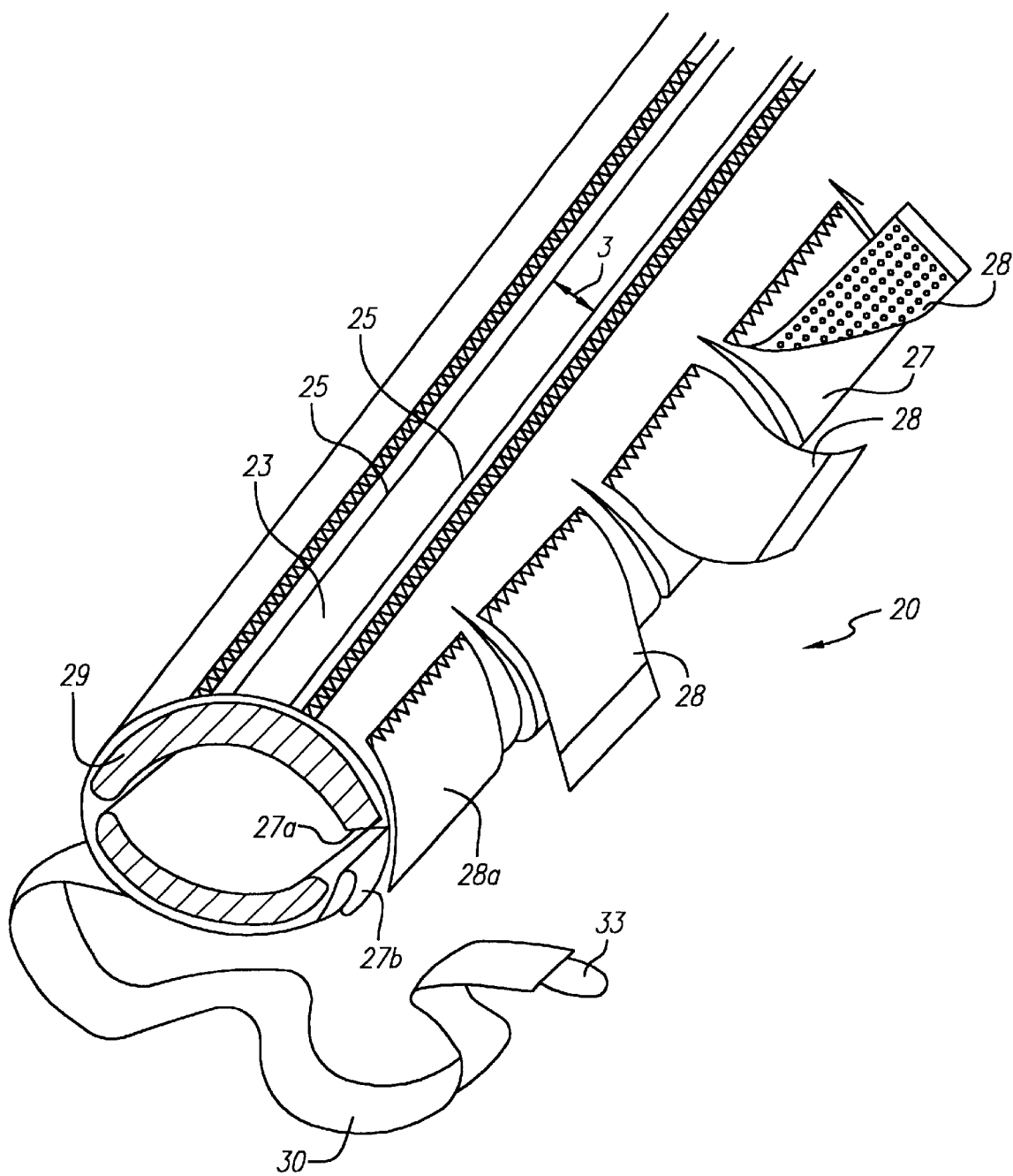
FIG. 12 is a perspective view of a portion of the compression device shown in FIG. 2.

FIG. 12 shows another view of the compression device 20, with sub-bands 27, hook tape fasteners 28, padding 29, elastic 23, indicia 25 in the form of lines, elastic wrap band 30 for wrapping hand or foot, and hook tape fastener 33 for attaching elastic wrap. In the figure, the first sub-band 27a has been pulled tight (in order to compress a body part that is not shown) and attached with fastener 28a, with the material of the sub-band 27a made into a fold 27b. The compression may be measured by determining the separation or interval 3 between the indicia 25 on the band 23.

In an alternative embodiment of the compression device shown in FIGS. 2, 11, and 12, darts or seams are sewn into the sheet 21 so as to enable the sleeve 24 conform to the bent shape of an arm at the elbow, the leg at the knee, or another jointed body part. Also, by varying the width of the sheet, the sleeve 24 would be formed to taper, or otherwise vary in circumference, in order to conform to the shape of the body part.

Figure 13:
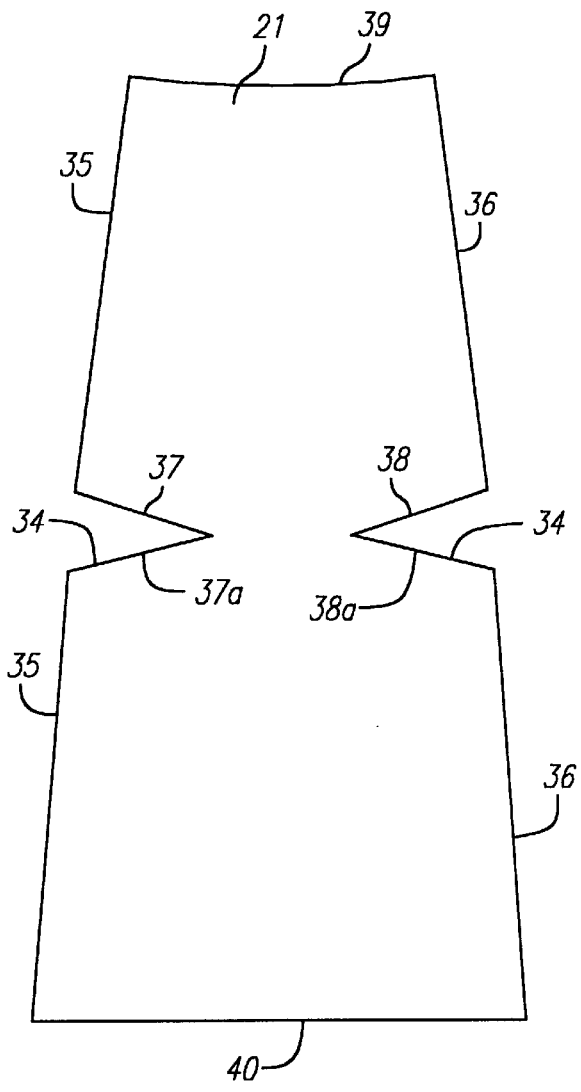
FIG. 13 is a view of a pattern of part of another preferred embodiment of the compression device according to our invention.
Figure 14:
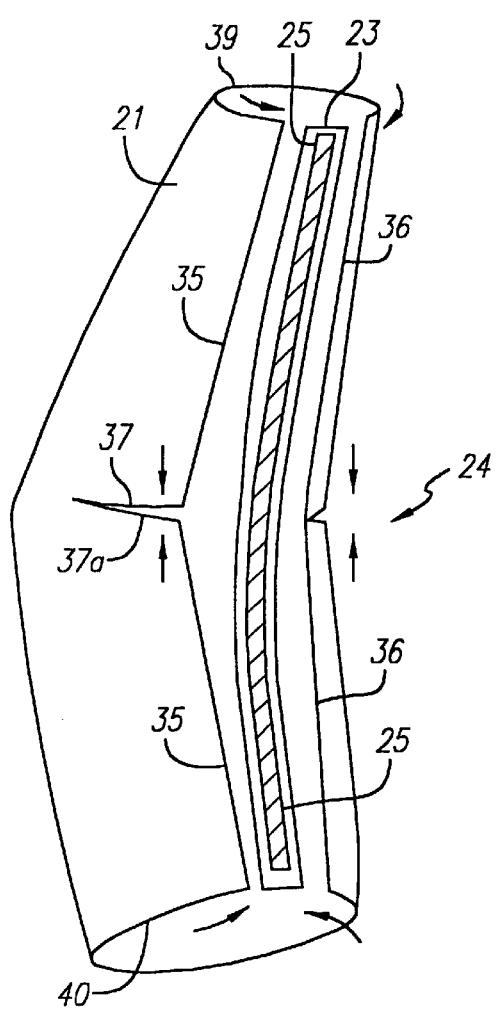
FIG. 14 is an exploded view showing the assembly of the compression device partly shown in FIG. 13.

FIG. 13 shows a flat sheet 21 of inelastic loop material with darts 34 cut into it. FIG. 14 shows the assembly of the sheet 21 into a sleeve 24. As edges 35 and 36 are wrapped around and towards each other, the darts 34 are closed by sewing edges 37 and 37a together and edges 38 and 38a together, thus creating a bend in the finished sleeve 24. A strip of elastic 23 with indicia 25 is sewn along edges 35 and 36, between edges 39 and 40, thus completing the sleeve 24. The sub-bands 27, although not shown in FIGS. 13 and 14, are added by making slits 26.

Figure 15:
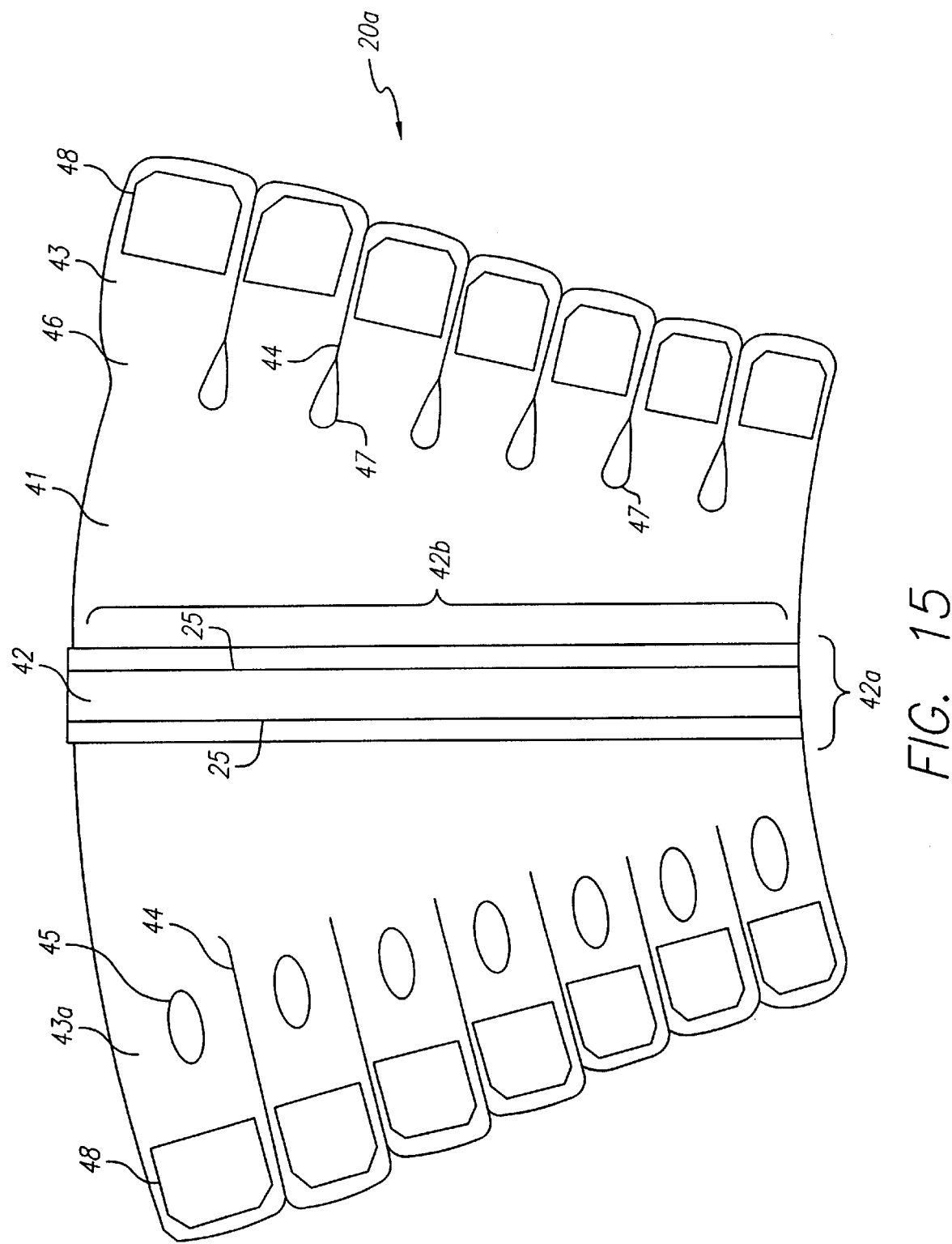
FIG. 15 is a view of another preferred embodiment of the compression device according to our invention.

FIG. 15 shows an alternate embodiment 20a of the compression device. A large sheet 41 largely made of substantially nonelastic material is wrapped around the body part. The sheet 41 contains a band portion 42 that is elastic over the entire width of its elastic axis. The elastic axis in this embodiment is along the length 42a of the band portion 42 and not its width 42b. The band portion 42 may be made of a Velcro-type loop material. Two or more parallel lines 25 are printed on the band portion 42 of the device, running along at least a portion of the width of the outer side of the band portion 42, and serve as indicia to be used with a card 7a–7c for determining compression.

At each end of the elastic axis of the band portion 42, the band portion 42 is attached along its width 42b to the substantially nonelastic material of the sheet 41. The sheet 41 is divided on either end into one or a plurality of sub-bands 43 and 43a, which extend outwardly from the band portion 42 in opposite directions in pairs. The length of the sub-bands 43 and 43a can vary, in order to accommodate body parts that taper or otherwise differ in circumference along their length. The sub-bands 43 and 43a can also have angles to them, to enable the garment to better conform to the limb. The sub-bands 43 and 43a are defined by slits 44 in the sheet 41. One of the sub-bands 43a of each pair includes a slot 45 to accommodate the opposite sub-band 43 in threaded, folded relationship to apply compression to the body part encompassed by the device 20a.

The sub-bands 43 that are threaded through the slots 45 may include portions or necks 46 of reduced width formed by cutting tear-drop shaped holes 47 at the base of each of the slits 44 separating the sub-bands 43. Such narrow width portions, however, are not essential if a sufficiently flexible and foldable fabric is used for the sheet 41.

The inner surfaces of the sub-bands 43 have hook surfaces 48 at or near their ends. The opposite sub-bands 43 of each pair are extended toward each other and one sub-band 43 of each pair is threaded through the slot 45 in the other sub-band 43a of the pair and then tightened to apply the desired compression to the body part. The inner hook surfaces 48 are then secured to the outer loop surface of the fabric of sheet 41 in order to anchor the sub-bands 43 in a tightened condition.

As the sub-bands 43 are tightened around the limb, one of the cards 7a–7c is held against the indicia 25 on the portion of the device 20a opposite the sub-bands 43, in order to determine what compression level has been obtained under that region of the device 20a, provided the circumference of the body part is known. The sub-bands 43 can be adjusted to obtain the desired compression, by lifting up the hook surfaces 48 of the two sub-bands 43 of the pair, adjusting the tension, then reattaching the two sub-bands 43 and using the card 7a–7c to re-read the compression. The card 7a–7c can be used to establish or verify equal or varying tension on the sub-bands 43 as necessary. As an example, the natural distal-to-proximal increase of circumference will automatically yield a gradient of compression running up the limb when each of the pairs of sub-bands 43 exerts equal tension (i.e., the indicia lines 25 are parallel), without the user having to set a different target compression for each pair of sub-bands 43.

The garment or device 20a is removed by separating the hook surfaces 48 of the sub-bands 43 from the outer loop surface of the sheet 41 and then unthreading the sub-bands 43 from each other.

Figure 16:
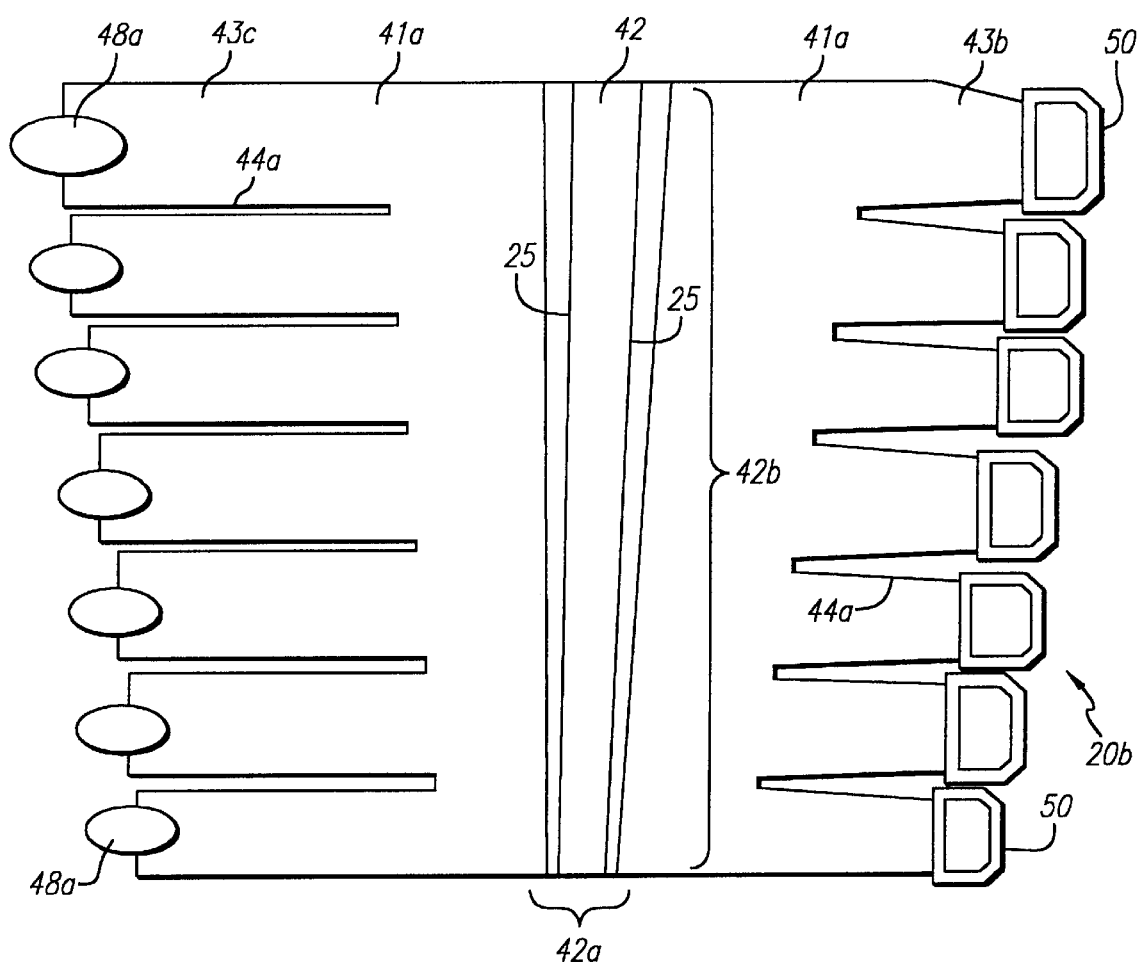
FIG. 16 is a view of a variant of the compression device shown in FIG. 15.
Figure 17:
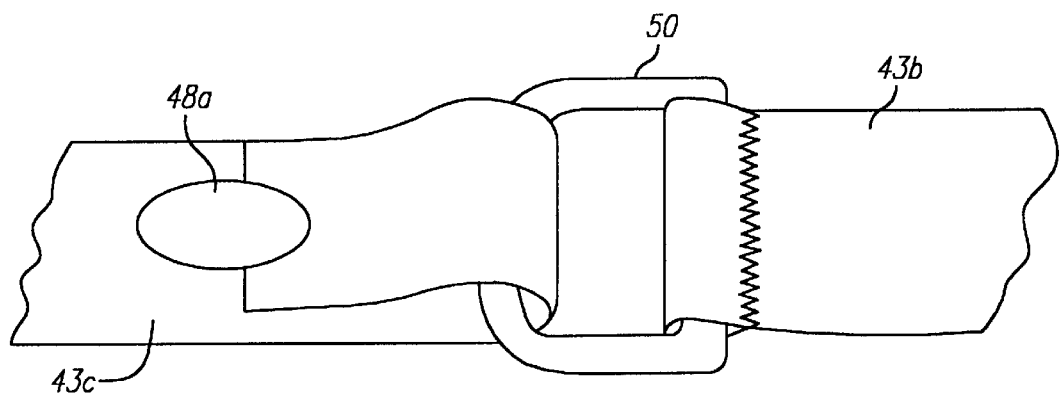
FIG. 17 is a view of a portion of the compression device shown in FIG. 16 showing how the members of a pair of opposing sub-bands are attached to each other.

FIGS. 16–17 show another embodiment 20b of the device as described in FIG. 15. differing only in that the opposing pairs of sub-bands 43b and 43c are attached using a D-ring system. FIG. 16 shows how this embodiment includes a large sheet 41a of substantially nonelastic material 41a, which is wrapped around the body part. At least a portion of the band 42 is elastic over the entire width of its elastic axis, which in this embodiment is the length 42a of the band 42 and not its width 42b. Two or more indicia lines 25 are printed on the band 42, running along at least a portion of the width of the band 42, and serve as indicia to be used with the card 7a–7c for determining compression.

At each end of the elastic axis of the band 42, the band 42 is attached along its width 42b to the sheet 41a. The sheet 41a is divided on either end into one or a plurality of sub-bands 43b and 43c that extend outward in opposite directions in pairs. The length of the sub-bands 43b and 43c can vary, in order to accommodate body parts that taper or otherwise differ in circumference along their length. The sub-bands 43b and 43c can also have angles to them, in order to enable the garment to better conform to the limb.

The sub-bands 43b and 43c are defined by slits 44a in the sheet 41a. One of the sub-bands 43b of each pair has a D-ring 50 sewn to its end. The outer surface of the other sub-band 43c in the pair has a fastener 48a made of a hook material at or near its end. The opposite sub-bands 43b and 43c of each pair are extended toward each other and one sub-band 43c of each pair is threaded through the D-ring 50 in the other sub-band 43b of the pair. Pulling away from the D-ring 50 to apply the desired compression to the body part then tightens the sub-band 43c.

FIG. 17 shows how the outer hook surface is then folded against the outer loop surface of the fabric of the sub-band 43c to anchor the sub-bands 43b and 43c in tightened condition. As the sub-bands 43b and 43c are tightened around the limb, the card 7a–7c is held against the indicia lines 25 on the elastic band 42 in order to determine what compression level has been obtained under that region of the sleeve 41a, provided the circumference of the body part is known. The sub-bands 43b and 43c can be adjusted to obtain the desired compression, by lifting up the hook surfaces of the fasteners 48a of the sub-band 43c, adjusting the tension, then reattaching the sub-band 43c to itself and using the card 7a–7c to re-read the compression.

The card 7a–7c can be used to establish or verify equal or varying tension on the sub-bands 43b and 43c as necessary. As an example, the natural distal-to-proximal increase of circumference will automatically yield a gradient of compression running up the limb if equal tension is exerted by the elastic band 42 at each height (i.e., the indicia lines 25 are parallel), without the user having to set a different target compression for each elevation on the band 42. The garment is removed by separating the hook surfaces of the fasteners 48a from the outer loop surface of the sub-bands 43c and then unthreading the sub-bands 43c from the D-rings 50.

The compression devices 20–20b shown in FIGS. 2, 11–17, and 20–21 could include additional features such as a longitudinally extending slide fastener, preferably mounted in the inelastic sheet component, to enable easier application or removal of the device. These devices could also include lacing in the inelastic sheet component for the purpose of tightening and conforming the device to a body part. The opposing members of pairs of sub-bands could be attached to each other by lacing for tightening and otherwise adjusting the compression provided by these sub-bands.

Figure 18:
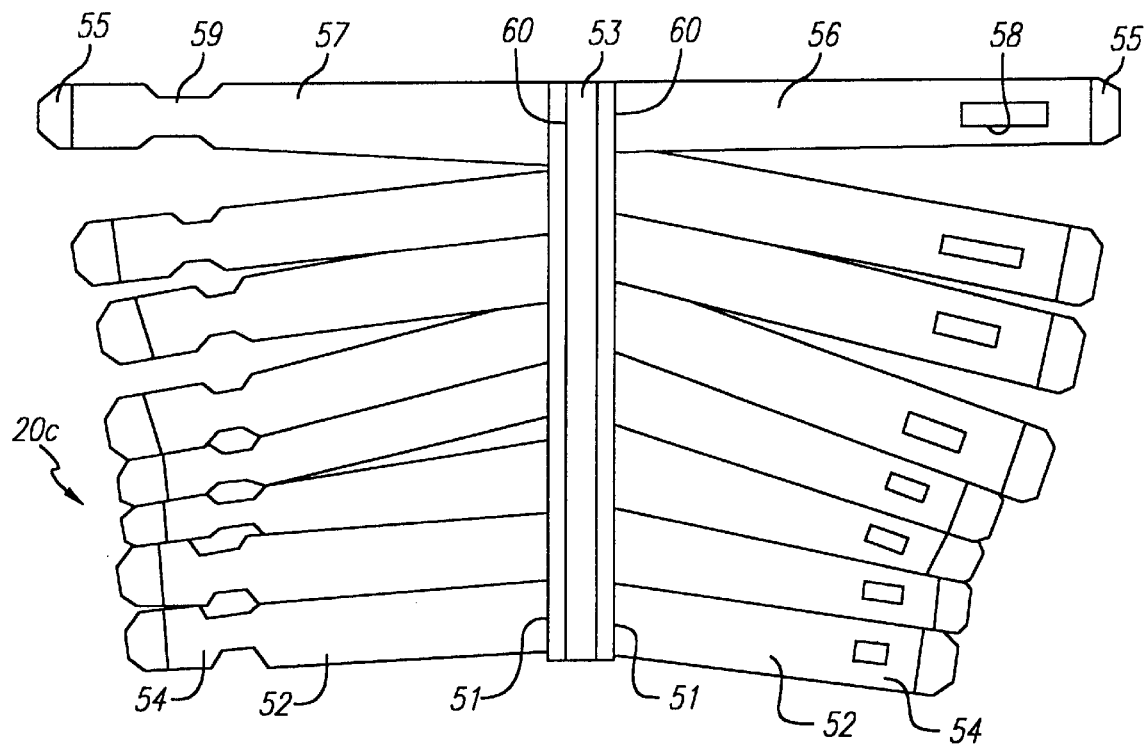
FIG. 18 is a view of another variant of the compression device shown in FIG. 15.

FIG. 18 shows a compression device 20c that is another variant of the compression device 20a shown in FIG. 15. The compression device 20c is formed by sewing or otherwise attaching the base ends 51 of opposing pairs of inelastic bands 52 to either side of an elastic band 53. The bands 52 are preferably made of a loop material. The elastic axis of the elastic band 53 runs between the members of the opposing pairs of bands 52. The base ends 51 of the bands 52 are therefore attached along the width of the elastic band 53, just as the inelastic sheet 41 is attached along the width of the elastic band portion 42 in the compression device 20a shown in FIG. 15.

The lengths of the members of the opposing pairs of inelastic bands 52 are selected to be long enough to surround an appropriate part of a limb. Each inelastic band 52 has a free end 54 to which is sewn a fastener 55. The fastener 55 is preferably made of a hook material for attachment to the loop material of the inelastic bands 52.

A female member 56 of a pair of opposing inelastic bands 52 will have a slot 58 through which the free end 54 of the corresponding male member 57 can be inserted in folded engagement. The male member 57 can have a narrowed neck 59 that will enable the male member 57 to fit within the slot 58 of the female member 56 (see FIG. 19). The fasteners 55 are used to attach the free end 54 of one member of the pair of opposing inelastic bands 52 to the other member of the pair of inelastic bands 52.

Indicia lines 60 are printed on the elastic band 53. The indicia lines 60 are parallel when the elastic band 53 is not under tension. A card 7a–7c is used to measure or predict the compression provided by each pair of opposing inelastic bands 52 to the limb, when the circumference is known, as in the compression device 20a shown in FIG. 15.

Figure 19:
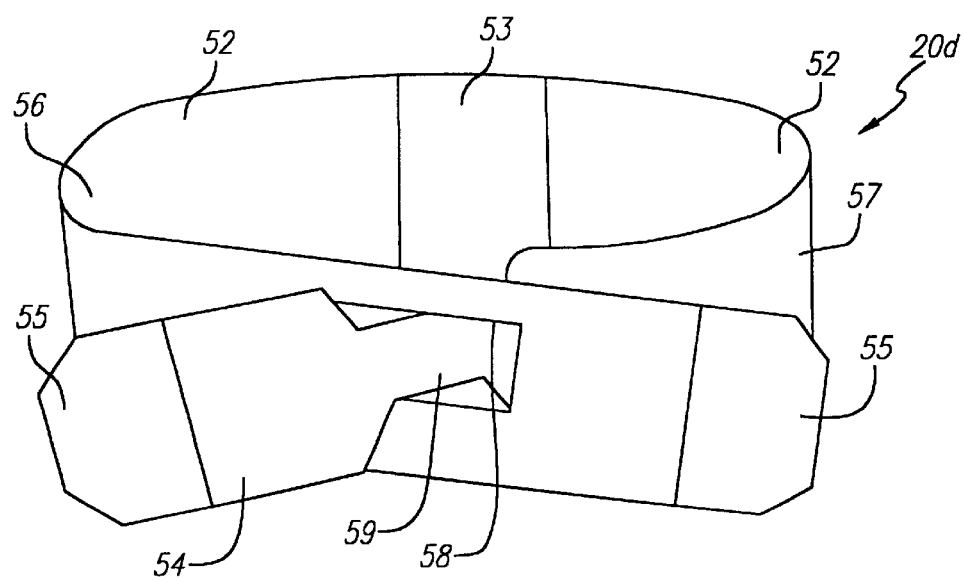
FIG. 19 is a view of a variant of the compression device shown in FIG. 18.

FIG. 19 shows a compression device 20d that consists of a single pair of opposing inelastic bands 52 attached to an elastic band 53. The free end 54 of the male member 57 of the opposing pair is shown inserted through the slot 58 of the female member 56. Indicia lines are printed on the elastic band 53 but are not visible in the view shown in FIG. 19.

Figure 20:
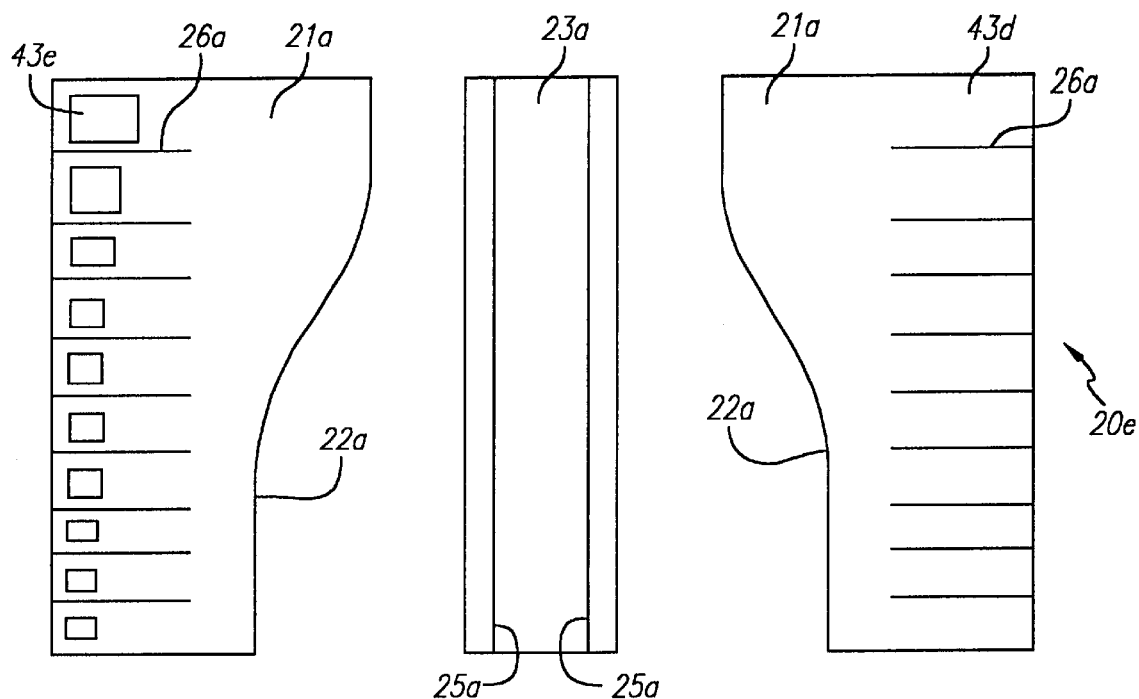
FIG. 20 is an exploded side view of another embodiment of the compression device according to our invention.
Figure 21:
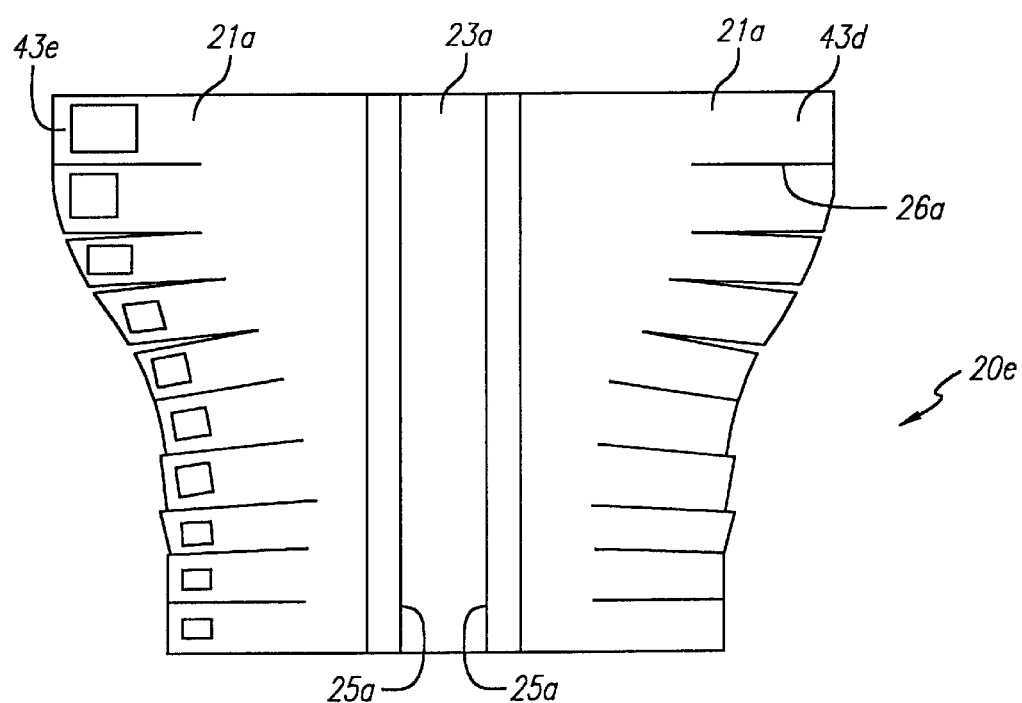
FIG. 21 is a side view of the compression device shown in FIG. 20, as assembled.

FIGS. 20–21 show a compression device 20e adapted for superior fit to any part of the body and superior comfort. The compression device 20e is comprised of three pieces of material that are attached to one another to form a single compression garment. An elastic band 23a runs vertically in order to form a moldable central area that enables the device 20e to conform to the desired body part. The elastic material used in the elastic band 23a preferably will stretch in all directions so that a maximum amount of flexibility is given to the device 20e, thereby allowing the device to conform to the body part as well as possible. Neoprene is a preferred one of many types of elastic material that may be used successfully as the material for the elastic band 23a.

The compression device 20a also has two sheets 21a made of substantially inelastic Velcro loop material that are attached to the sides of the elastic band 23a. These sheets 21a may be fastened to the elastic band 23a by any means that does not affect the fit of the device 20e. For example, they may be either sewn to the elastic band 23a or attached with overlapping Velcro strips. The two sheets 21a have slits 26a cut into each of them from one side in order to form a plurality of sub-bands 43d and 43e. The parallel slits 26a can be of any length and are cut in the direction that the fabric is strongest and the least elastic.

Preferably, the sheets 21a are aligned so that the constituent fibers of the sheets 21a are directed so as to minimize stretch in the sheets 21a in the direction of the elastic axis of the elastic band 23a. In other words, the elasticity of the sub-bands 43d and 43e (see below) in their wrapping direction is minimized so that any change in dimension is due to stretch in the elastic band 23a.

The sides 22a of the sheets 21a are opposite the sides divided into the sub-bands 43d and 43e and are cut to a curve that depends on the shape and size of the body part the device 20e is to fit. The shape of this curve will determine the angles at which the sub-bands 43d and 43e are initially set and will bias the sheets 21a into a three-dimensional curvature that better fits a body part. The elastic band 23a will also play a factor in determining the angles of the sub-bands 43d and 43e once the device 20e is applied to the body part. The sides 22a of the sheets 21a are attached to the vertical sides of the elastic band 23a.

Figure 24:
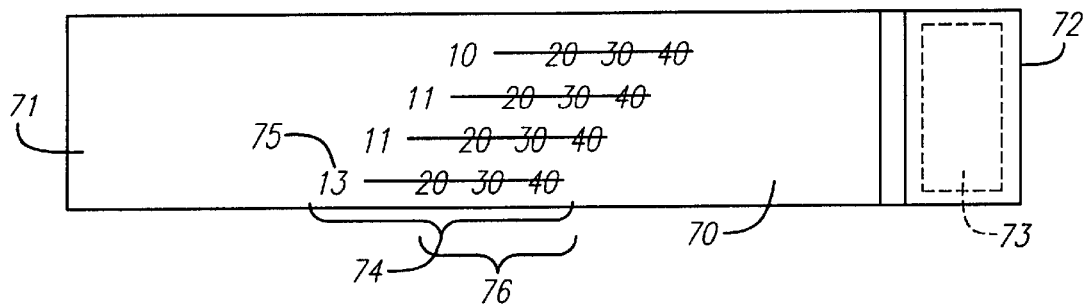
FIG. 24 is a view of a variation of the compression device shown in FIG. 22.
Figure 25:
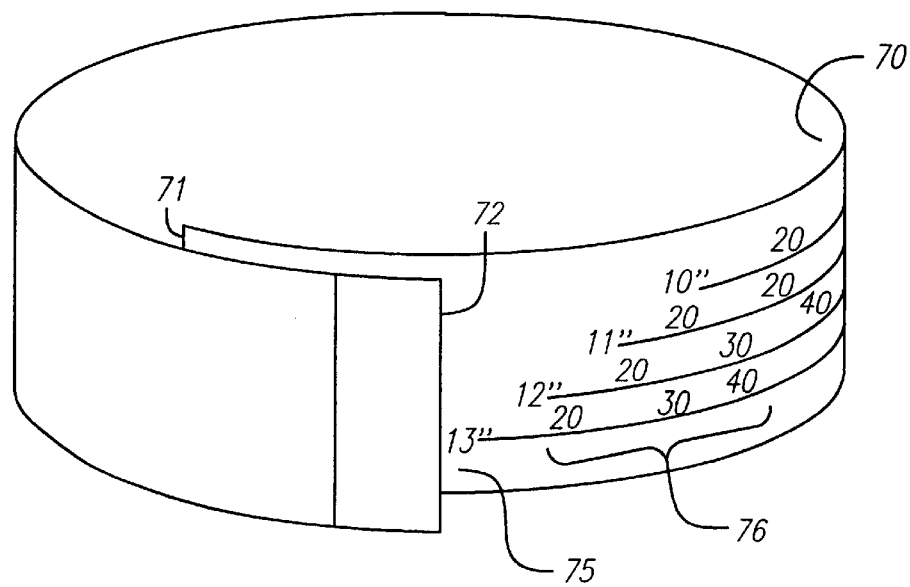
FIG. 25 is another view of the compression device shown in FIG. 24.
Figure 26:
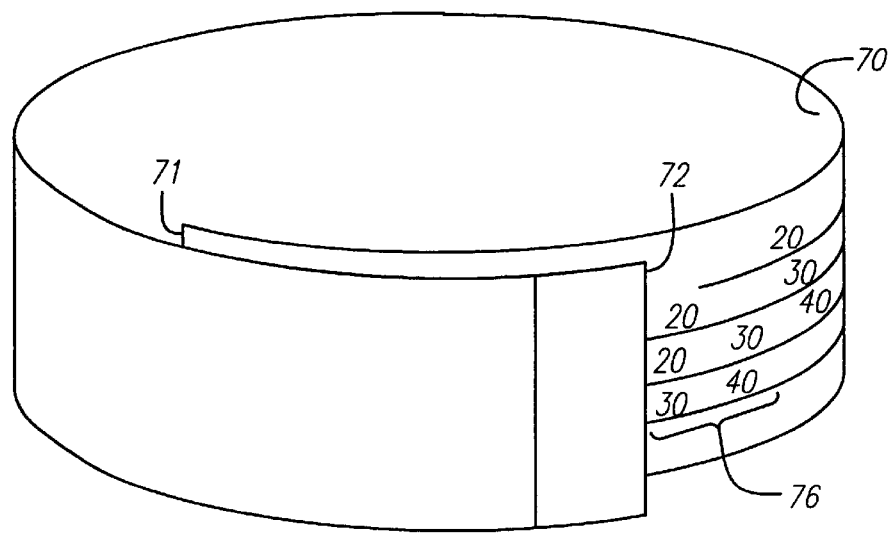
FIG. 26 is another view of the compression device shown in FIG. 24.

The sub-bands 43d and 43e could be wrapped around the body part, tightened, and fastened to each other by Velcro hook and loop materials as in the system of interlocking bands of the devices shown in FIGS. 15, 18 or 19, the push pocket system of FIGS. 24–26, or any other system described in this specification and any equivalent.

The elastic band 23a may be used in connection with the compression measuring system described in connection with FIGS. 2–19 by adding indicia lines 25a. The device 20e could also be used in connection with the compression measuring systems described in connection with FIGS. 1 and 22–42 by providing indicia on the sub-bands 43d and/or 43e (not shown).

Compression devices according to the present invention include embodiments that do not require the use of a card 7a–7c or other such separate device in order to measure the compression. The means for measuring the stretch of the elastic component of a compression device and the means for correlating the stretch of the device to the compression that it provides are markings applied directly to the band, sleeve or garment of the compression device. The device itself therefore is used to measure the amount of compression that is provided to the limb or other body part.

FIGS. 22–23 show one such compression device that is a substantially elastic band 61. The band 61 preferably is made of an elastic loop material. The band 61 has a base end 62 and a free end 63. A fastener 64 is sewn to the underside or inner side of the band 61 (shown in hidden line) and is preferably made of a hook material that will removeably attach to the loop material of the band 61. Compression measurement indicia 65 are printed on a central region of the exterior or outer side of the band 61.

In this embodiment the indicia 65 each consist of pairs of markings 66 and 67. The markings 66 are circumferences (shown in inches although metric units could be employed) and the markings 67 are compression (shown in millimeters of mercury although other measures of pressure could be employed). FIG. 23 shows how the indicia are used to measure or predict the compression applied by the band 61 to the limb or body part.

In FIG. 23 the band 61 is shown to be wrapped around a body part (body part not shown). The band 61 is wrapped around the body part so that the band 61 wraps over the base end 62 of the band 61. The fastener 64 attaches the free end 63 to the outer surface of the central region of the band 61 in the vicinity of the indicia 65. The user observes where the edge or other specified portion of the free end 63 of the band 61 falls on the central region of the band 61 and thus which indicia 65 are contacted by the free end 63. Having previously measured the circumference of the body part, the compression under the band 61 is easily determined by identifying the compression marking 67 associated with the circumference marking 66 that is closest to the measured circumference.

The position of the edge or other specified portion of the free end 63 of the band 61 (and thus the marking it reaches) is a measure of the stretch of the band 61 and thus the tension it experiences. The tension is converted to compression by consideration of the circumference, the amount of overlap, and so forth as described above in connection with the cards 7a–7c shown in FIGS. 7–9 and below in the section entitled "Explanation of Engineering Principles."

The indicia 65 could consist of pressure and/or circumference measurements themselves, or simplified indicators (e.g. A, B, C, and so forth) that could be referenced to a table that would give the compression based on the measured circumference of a body part and the indicator read from the band 61.

The band 61 can be adapted for use on any body part by being made and calibrated to fit different sizes of limbs. Two or more of the bands 61 could be joined to make a garment for a limb similar to those in FIGS. 3, 4, 10, and 18 but without the need to measure the interval between indicia with a card 7a–7c.

FIGS. 24–26 show another embodiment of a compression device. A substantially elastic band 70 has indicia printed thereon for measuring both the circumference of the body part and the compression provided for a given circumference.

As with the band 61 shown in FIGS. 22–23, the band 70 preferably is made of substantially elastic loop material. The band 70 has a base end 71 and a free end 72. The free end 72 has a fastener 73 sewed on its underside for removable attachment of the free end 72 to the outer side of the band 70 (the outer side of the band 70 is shown in FIG. 24). The fastener 73 is preferably made of a hook material.

One or more scales 74 are printed on the outer side of the band 70. Each scale 74 is to be used for a specific circumference of the limb or body part that is to be compressed by the band 70. (Alternatively, each scale 74 could be used for a particular compression that is to be achieved and the individual markings correspond to different circumferences, although this variation is not shown in FIGS. 24–26.) Each scale 74 has a circumference marker 75 stating the circumference for which the scale 74 is calibrated. The circumference marker 75 is located at a distance from the edge or other specified portion of the free end 72 along the elastic or longitudinal axis of the band 70, in a circumferential direction with respect to the body part that is equal to that circumference when the band 70 is not under tension. A series of marks 76 corresponds to various non-zero compression levels. The circumference marker 75 is also the zero compression mark for that circumference.

The band 70 is applied to the body part as follows. In a first step the band 70 is wrapped around the body part such that the free end 72 wraps around and over the base end 71 of the band 70. The band 70 is initially wrapped only loosely so that no compression is applied to the body part. In the next step the user observes which of the circumference markers 75 the edge or specified portion of the free end 72 touches. In a third step the user employs the scale 74 corresponding to the observed marker 75 in order to set the compression to a desired amount. The user stretches and reapplies the band 70 so that the edge or specified portion of the free end 72 aligns with the desired one of the compression marks 76 on the scale 74. The user, in a fourth step, attaches the free end 72 of the band 70 to the outer surface of the band 70.

The band 70 is shown in FIG. 25 to be in the initial step of being wrapped loosely. The user will observe that the free end 72 aligns with the circumference marker 75 having the stated value "13." The user now knows that the circumference of the body part is 13 inches at this point.

The band 70 is shown in FIG. 26 to be stretched (and thus tensioned) to a compression mark 76 having the stated value "30." This corresponds to a compression of 30 millimeters of mercury. A compression of approximately 30 millimeters of mercury is being applied to the body part. Assuming that this is the desired compression, the user will then attach the free end 72 to the outer surface of the band 70 using the fastener 73.

The location of the compression marks 76 within the scales 74 is primarily based on the elasticity of material being used, as described below. Adjustments to the locations of the compression marks 76 may be made for various reasons. These reasons include the necessity of accounting for angles in the orientation of the band 70, layering of the band 70 over itself or over other bands, predicted changes in the elasticity of the fabric due to the passage of time, use or environmental factors, friction between the band 70 and the substrate (such as the body part itself or a stockinet), and to create a gradient of compression in a series of bands 70. These adjustments can be determined empirically as discussed below in the section of this specification entitled "Explanation of Engineering Principles."

Circumference markers 75 could be printed on the bands or sub-bands of the compression devices shown in FIGS. 2–5 and 10–19 for use in measuring circumference in the manner described above.

FIGS. 27–28 show a compression device that operates according to the same principles as the band 70 shown in FIGS. 24–26. A band 80 has two sets of scales 81 and 82, one set of scales adjacent either end of the band 80, so that each end of the band 80 is aligned against the scales 81 or 82 adjacent the opposite end. The scales 81 and 82 have the same format as the scales 74 in the embodiment of a compression device shown in FIGS. 24–26.

The band 80 has a slot 85 near the end 83 sized to accommodate the opposite end 84 when the end 84 is inserted through the slot 85, as shown in FIG. 28. The band 80 may have reduced width at a neck 86 near the end 84 in order to better fit into the slot 82. The user can observe both ends 83 and 84 of the band 80 and both sets of scales 81 and 82.

The user measures the circumference of the body part when the band 80 is loosely wrapped around the body part by observing which circumference markings 81a and 82a are aligned with the ends 84 and 83, respectively. The user then selects the corresponding ones of the scales 81 and 82 for the circumference thereby measured. Finally, the user pulls the ends 83 and 84 apart until they align with the compression marks 82b and 81b, respectively, for the desired compression. Hook material fasteners sewn to the underside of the band 80 adjacent each of the ends 83 and 84 (not shown) are then used to detachably secure each of the ends 83 and 84 to the outer surface of the band 80.

Figure 29:
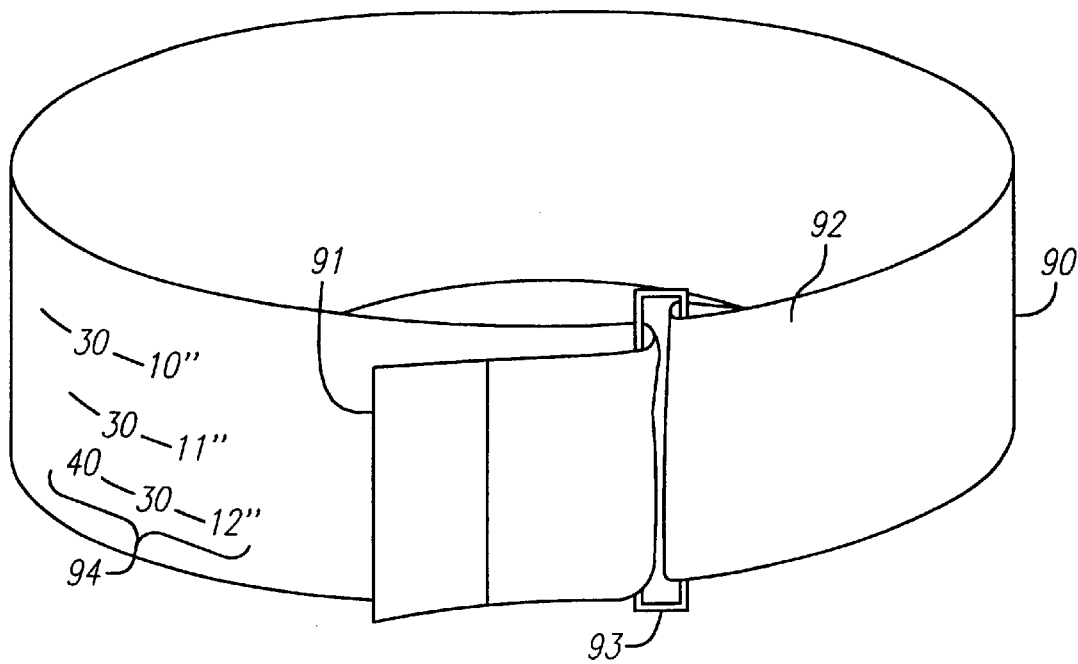
FIG. 29 is a view of a variation of the compression device shown in FIGS. 24–26.
Figure 30:
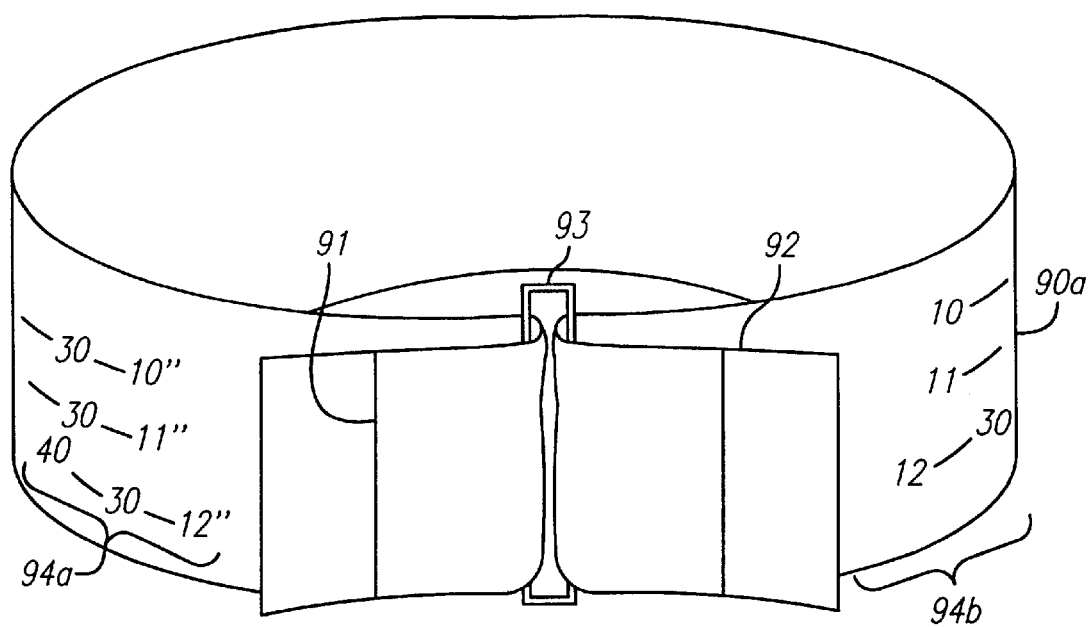
FIG. 30 is a view of a variation of the compression device shown in FIGS. 27 and 28.

FIGS. 29–30 show two more embodiments of a compression device that operates according to the same principles as the band 70 shown in FIGS. 24–26, in which D-rings are employed. FIG. 29 shows a band 90 that has a first end 91 (the free end in this embodiment) that is wrapped around a limb (not shown) and inserted through a D-ring 93 attached to a second end 92 (the base end in this embodiment) of the band 90. The free end 91 is folded back on itself and the set of scales 94 used as described in connection with FIGS. 24–26. A fastener preferably made of hook material is sewn to the outer side of the band 90 (not shown) in order to secure the band 90 in place at the desired compression.

The elastic band 90a shown in FIG. 30 is similar to that of FIG. 29. However, both ends 91 and 92 are inserted through the D-ring 93 and folded back against separate sets of scales 94a and 94b. The user then measures the circumference of the body part and sets the compression using the procedure described in connection with FIGS. 27–28.

Figure 31:
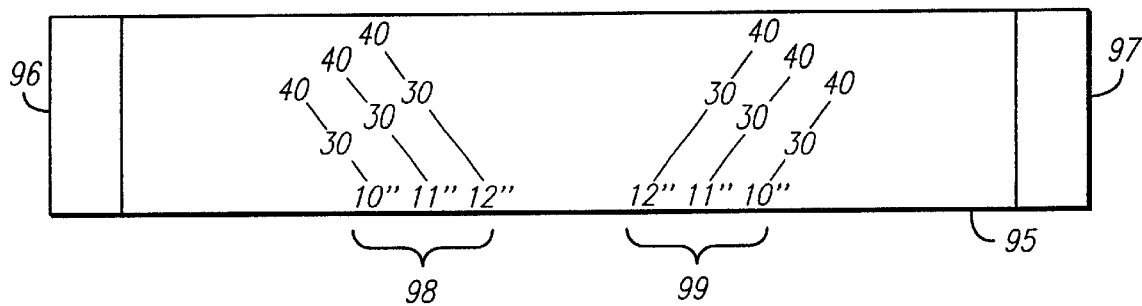
FIG. 31 is a view of another preferred embodiment of the compression device according to our invention.
Figure 32:
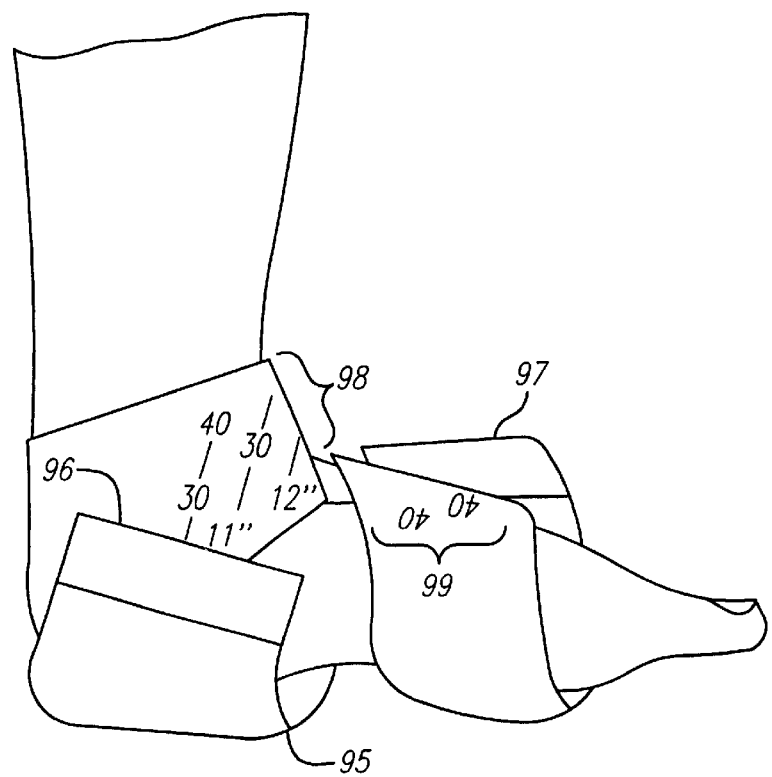
FIG. 32 is another view of the compression device shown in FIG. 31.

FIGS. 31–32 show another embodiments of a compression device that operates according to the same principles as the band 70 shown in FIGS. 24–26 but is adapted to be used with body parts having angles that require considerable spiraling of the band.

Scales 98 and 99 are printed at a slant adjacent one or both ends 96 and 97 of the outer surface of a band 95 (see FIG. 31). As shown in FIG. 32, the band 95 is spiraled around a body part (ankle and foot) and the two ends 96 and 97 are attached to the outer surface of the band 95, preferably by means of sewn-on hook material fasteners (not shown). The scales 98 and 99 are each printed at an angle that will permit the sets of scales 98 or 99 to be used as described in connection with FIGS. 24–26 26 when the end 96 or 97 meets the band 95 in the vicinity of the scales 98 and 99 at an angle, as illustrated in FIG. 32.

Each half of the band 95 is referenced against itself. The exact position of the device on the body part therefore does not affect the accuracy of the measurement.

Compression devices using the principles employed in the bands described in connection with FIGS. 24–32 could have many different embodiments. Such compression devices could be a single band, a series of independent bands, a series of bands attached at their bases or along a portion of their lengths (such as the format of the devices shown in FIGS. 3, 4, 10 and 18), or a sleeve having a band that has been slit or otherwise divided into sub-bands (such as the format of the devices shown in FIGS. 2 and 10–17; the sub-bands, however, would be made of elastic material and would have scales printed on them as in the embodiments).

Compression devices according to the present invention require the tightening of straps, band, sub-bands and the like in order to establish tension in the material of the device along a circumference of the body part or limb. This will require pulling or pushing on the free ends of straps, bands, or sub-bands or on tabs attached to these components. The user will have to grasp the free ends or tabs with his or her fingers and pull or push. This will require a certain amount of finger dexterity and strength. Persons suffering from a circulatory disorder and possibly some other disability may have some difficulty pulling or pushing with the force necessary to achieve a good compression yet retaining their grip on the free end or tab.

Accordingly, the present invention provides a pocket that may be attached to a free end or tab of a strap, band or sub-band or other portion of the device for assisting the user to push or pull the free end or tab with his or her fingers. This pocket may be used with any of the compression devices shown and described in this specification.

Figure 33:
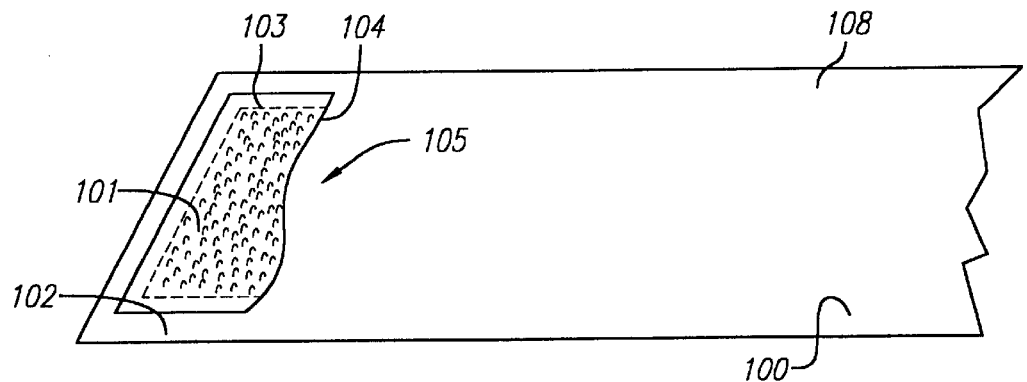
FIG. 33 is a perspective view of a portion of another preferred embodiment of the compression device according to our invention.

FIG. 33 shows a portion of a one-band compression device according to the invention, such as that shown in FIG. 5 or in FIG. 24, having an elastic band 100 (no indicia or markings are shown in order to simplify the diagram). The elastic band 100 has a pocket 101 sewn at an end 102 of the band 100 to serve as an aid when tightening the band 100. This is especially useful for persons who lack finger mobility, such as those persons suffering from arthritis, and cannot easily grasp bands or sub-bands between thumb and forefinger in order to pull on the band or sub-band. The pocket helps any person to tighten a band or sub-band in any compression device disclosed in this specification or, for that matter, any device or garment applied to the body.

The band 100 can be made of a loop material, with loop on both the top and bottom surfaces. In the embodiment shown in FIGS. 33–34, the pocket 101 is made of a hook material on its outward face. The pocket 101 is attached by sewing to the band 100 along its three edges 103, with the fourth edge 104 open, creating a space 105 into which a portion of the hand or one or more fingers can be inserted.

Figure 34:
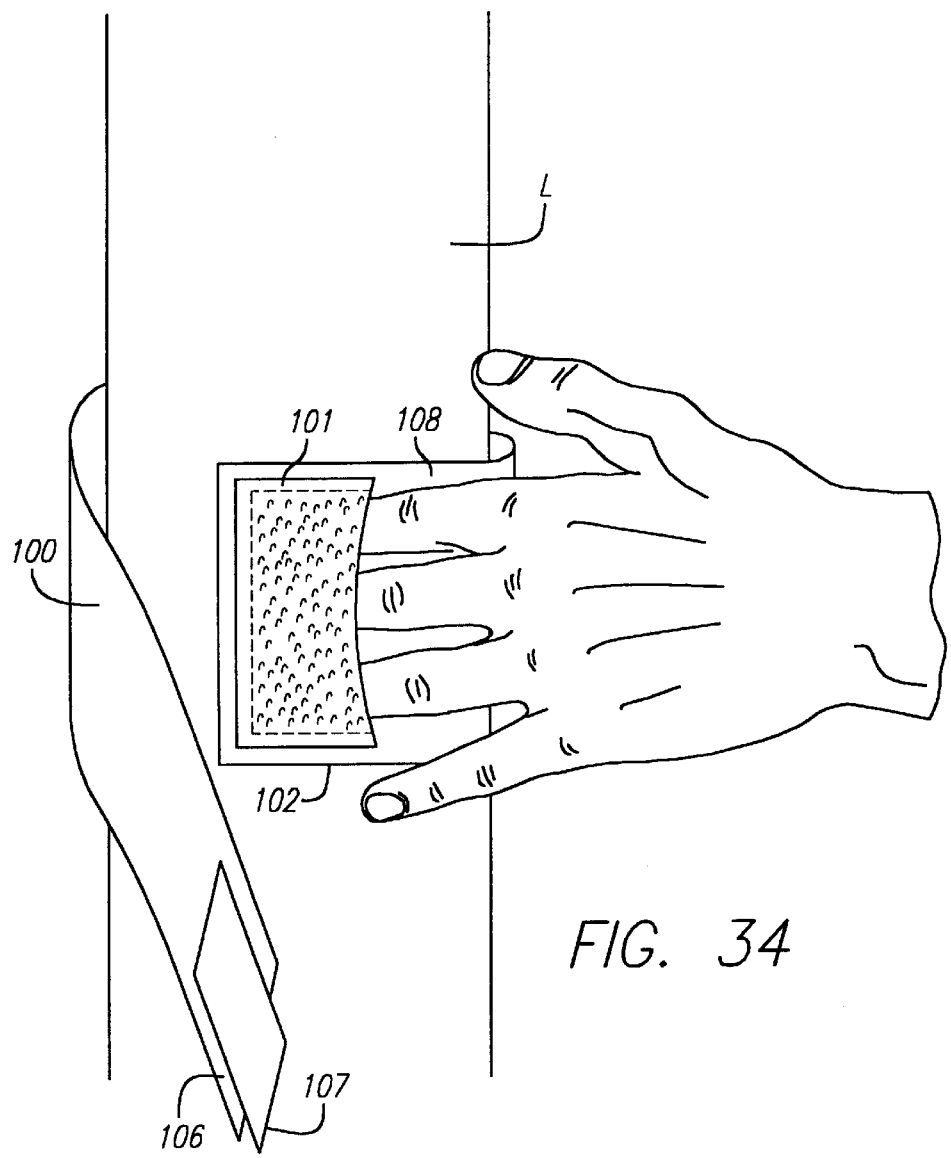
FIG. 34 is a perspective view of the compression device shown in FIG. 33.

FIG. 34 shows the pocket 101 in use: the band 100 is wrapped around a body part L with one or more of the fingers of one hand being inserted in the pocket 101. The user can either push his or her fingers into the pocket 101 as shown in FIG. 34 or can hook his or her fingers into the pocket 101 and pull (not shown) on the pocket 101 to urge the end 102 in the desired direction. The end 102 of the band 100 with the pocket 101 is tightened by pushing (or pulling) the fingers into the pocket 101 and tucking the end 102 under the opposite end 106 of the band 100. At the same time, the opposite end 106 is pulled tight and wrapped over the pocket 101. The hook material of the pocket 101 will help anchor the pocket 101 to the inside face of the outer and opposite end 106 of the band 100. A fastener 107, made of a hook material, is used to secure the end 106 to the loop material of the outside surface 108 of the band 100.

In another embodiment of the invention (not shown), the pocket 101 can be made of a non-hook material, and the inward pressure of the band can be sufficient to anchor the end in place. As the hand is pulled out and away from the pocket 101, the opposite end 106 of the band 100 is brought down and attached to the outer surface 108 of the band 100 using the fastener 107.

Figures 37, 38:
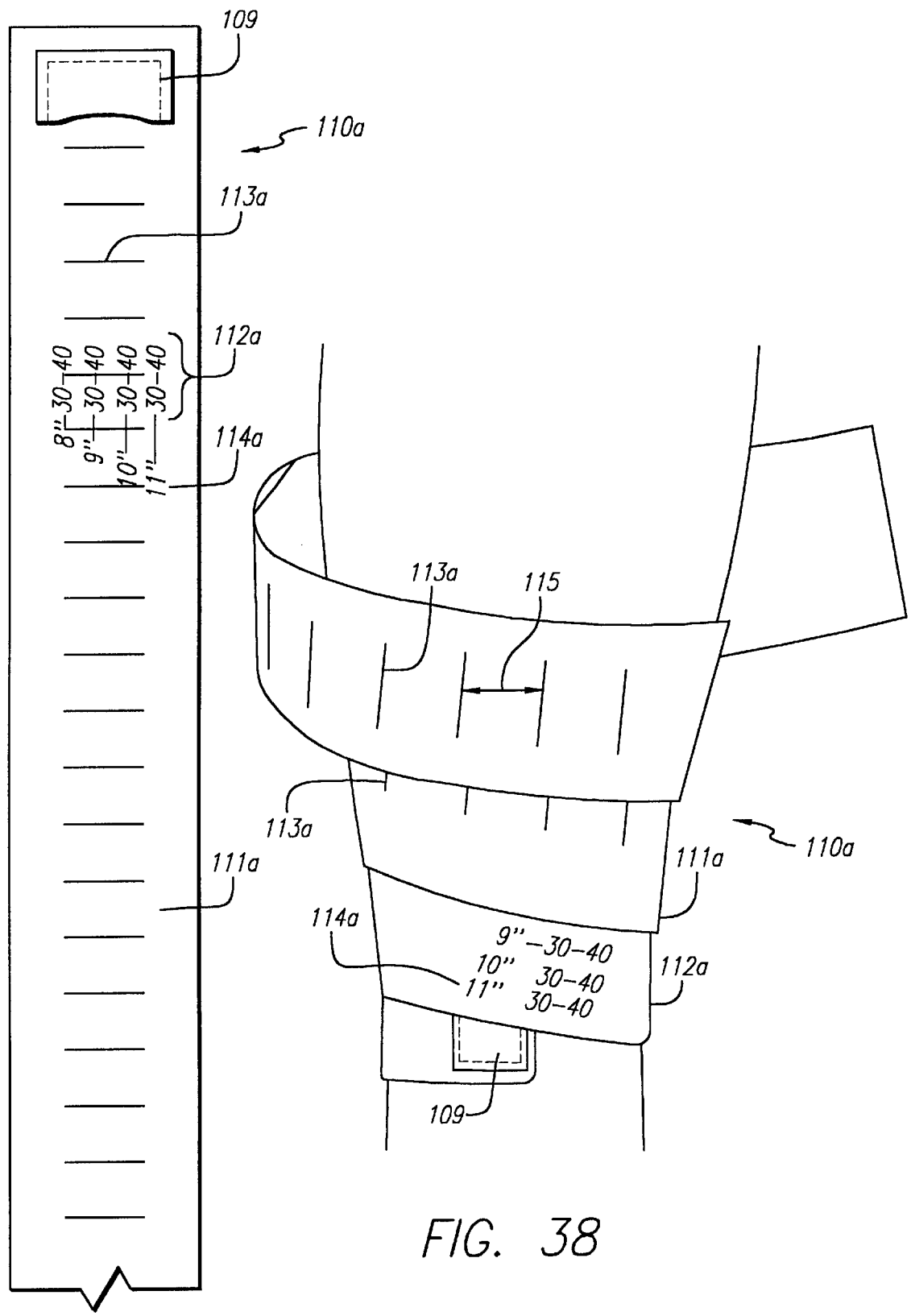
FIG. 37 is a side view of another embodiment of the compression device according to our invention.
FIG. 38 is a perspective view of the compression device shown in FIG. 37, being placed on the lower leg of a person.
Figure 39:
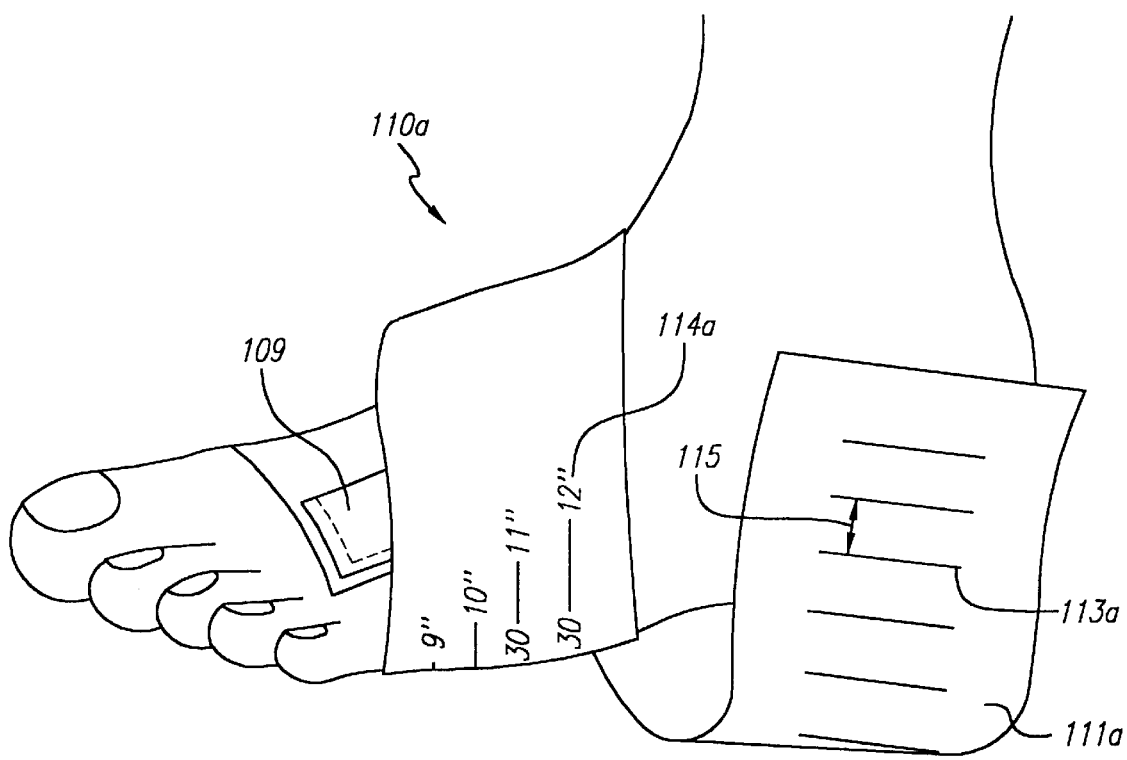
FIG. 39 is a perspective view of the compression device shown in FIG. 37, being placed on the foot of a person.

FIGS. 35–39 show two similar embodiments 110 and 110a of our compression device, consisting of a single band 111 or 111a that is elastic along at least a portion of its length, and that can be wrapped in spirals around a body part (as shown in FIGS. 36, 38, and 39). One or more sets of scales 112 or 112a would be printed on the band 111 or 111a, so that when the band 111 or 111a is stretched to the appropriate mark on the appropriate scale the correct compression is obtained under the band 111 or 111a. The bands 111 or 111a can be provided with pockets 109 for easier application, as described above in connection with FIGS. 33 and 34.

In the embodiment 110 shown in FIGS. 35 and 36, multiple sets of scales 112 are printed along the length of the band 111, such that when the band 111 is spirally wound about the body part, the scales fall at different elevations on the body part (see FIG. 36). The scales 112 can be similar to those used on the devices shown in FIGS. 19–21. Each set of scales 112, in addition to the scales themselves, would have a reference marker 113 against which the scales 112 are read. For example, the band 111 is applied by at first loosely wrapping the band 111 around the body part to determine the circumference of that part by observing which circumference marking 114 is contacted by the reference marker 113. The band 111 then is stretched until the desired compression level is reached on the scales 112 adjacent to the contacted circumference marking 114, which is the scales 112 corresponding to the measured circumference.

The band 111 is then held in place while a second turn is made around the body part, partially overlapping the first turn. As with the first, it is wrapped loosely at first to determine the circumference, and the band 111 is reapplied by stretching it to the desired compression level on the scales 112 corresponding to the measured circumference. This procedure is repeated with consecutive turns around the body part, until coverage is complete. The scales 112 can be calibrated such that each scale 112 yields lower actual compression values than the previous scale 112, enabling a gradient of compression along the length of the body part.

In another embodiment 110a of the device, shown in FIGS. 37–39, one or more sets of scales 112a are printed on the band 111a. A series of lines or other markings 113a are printed on the band 111a at fixed intervals along the entire length of the band 111a. When the band 111a is applied, an initial single turn around the body part is made, and the scale 112a is used to set the stretch of the band 111a, based on the desired compression level and measured body part circumference. The remainder of the band 111a is then applied so that the spacing between successive repeating lines/markings 113a is consistent with the spacing at the first turn of the band 111a around the body part. In this way, the stretch of the band 111a is kept constant along the length of the band 111a.

An example of the application of the embodiment 110a of the compression device according to our invention is a band 111a that provides compression to the lower leg as shown in FIG. 38. The band 111a is started at the ankle, where it is first wrapped loosely around the ankle and the circumference is measured using the circumference markings 114a. The band 111a then is wound back off the ankle, and pulled to the mark on the scale 112a corresponding to the desired compression level for the measured circumference. The band 111a then is wrapped in additional turns around the rest of the lower leg, using the repeating reference markings 113a to maintain a consistent tension by keeping the spacing 115 between successive reference markings 113a at the same length.

When applied as described above, the band 111a has a consistent tension along its entire length. On a limb with a fairly normal taper, this consistent tension will result in a gradient of compression going up the limb.

Another example is an application of the embodiment 110a of the compression device according to our invention is a band 111a that provides compression to an ankle as shown in FIG. 39. The band 111a is first wound around the base of the toes, where it is first wrapped loosely and the circumference of the foot is read. The band 111a is then wound back off, and re-pulled to the mark on the scale 112a corresponding to the desired compression level and circumference. The band 111a is then wrapped in additional turns around the rest of the foot and ankle, using the repeating reference markers 113a to maintain a consistent tension. The calibration of the scale 112a used at the initial portion of the band 111a can be adjusted to account for the complex layering and angles that occur when wrapping the ankle.

A pocket 109 can be used at the base of the band 111 or 111a to enable the end with the pocket 109 to be pushed/pulled tight under the second layer of wrapping of the band 111 or 111a.

Figure 40:
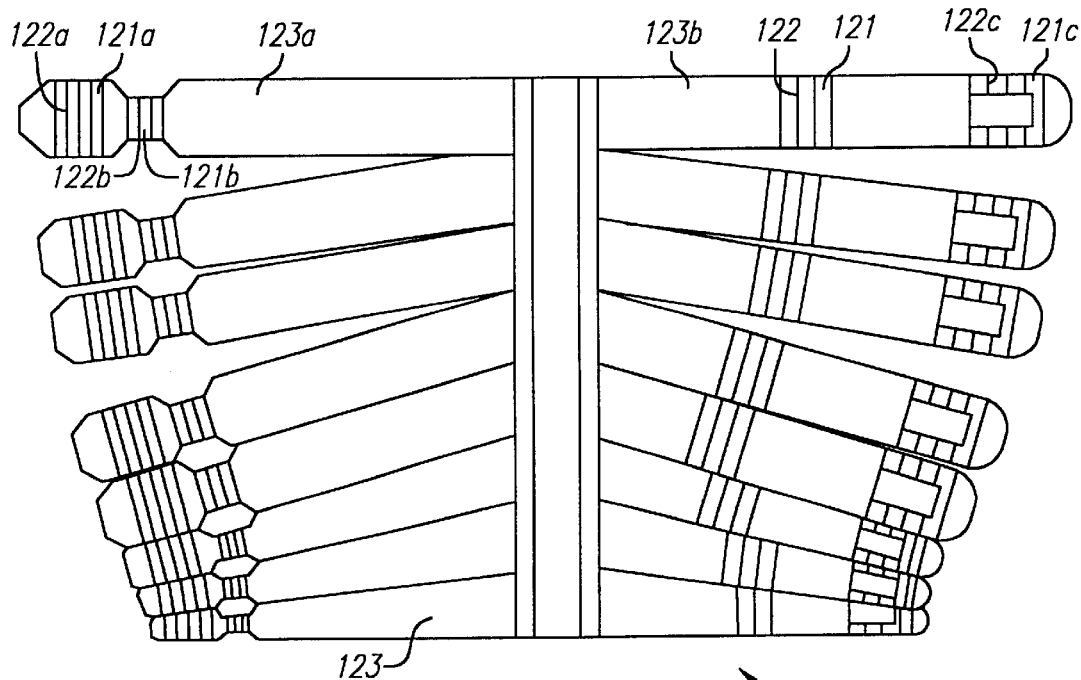
FIG. 40 is a side view of another embodiment of the compression device according to our invention.

FIG. 40 shows an embodiment 120 that is a variation of the compression device shown in FIG. 18. Embodiment 120 shows how the elastic portion of a compression device according to the present invention can be at any region of the device. In embodiment 120 an elastic band 121 with indicia lines 122 forms a section of the sub-bands 123. An elastic band 121a with indicia lines 122a forms a part of the ends of the sub-bands 123. Furthermore, an elastic band 121b with indicia lines 122b is placed at the narrow neck portion of the male sub-band 123a of each pair of the sub-bands 123. An elastic band 121c with indicia lines 122c is employed at either side of the slot in the female sub-band 123b. The locations of the elastic bands 121b or 121c permit the indicia lines 122b or 122c to be visible when the user has inserted the male sub-band 123a through the slot in the female sub-band 123b. The compression under each sub-band 123 can be measured by measuring the circumference and using a card such as those shown in FIGS. 7–9, as explained earlier, a gradient of compression can be obtained by using the card to establish uniform stretch on each of the sub-bands 123.

In the cases where the elastic band and indicia lines are at the neck or slot of the sub-bands 123, the calibration of the compression measuring card to be made to account for the difference in extension or stretch caused by tension in the narrow elastic portion of the sub-band 123 compared to the wider portion of the sub-band 123 where the compression is actually be applied.

The alternative placements of the elastic bands described above in connection with FIG. 40 could be applied to the embodiments of our compression device shown in FIGS. 2, 10–19, and 41–42.

Figure 41:
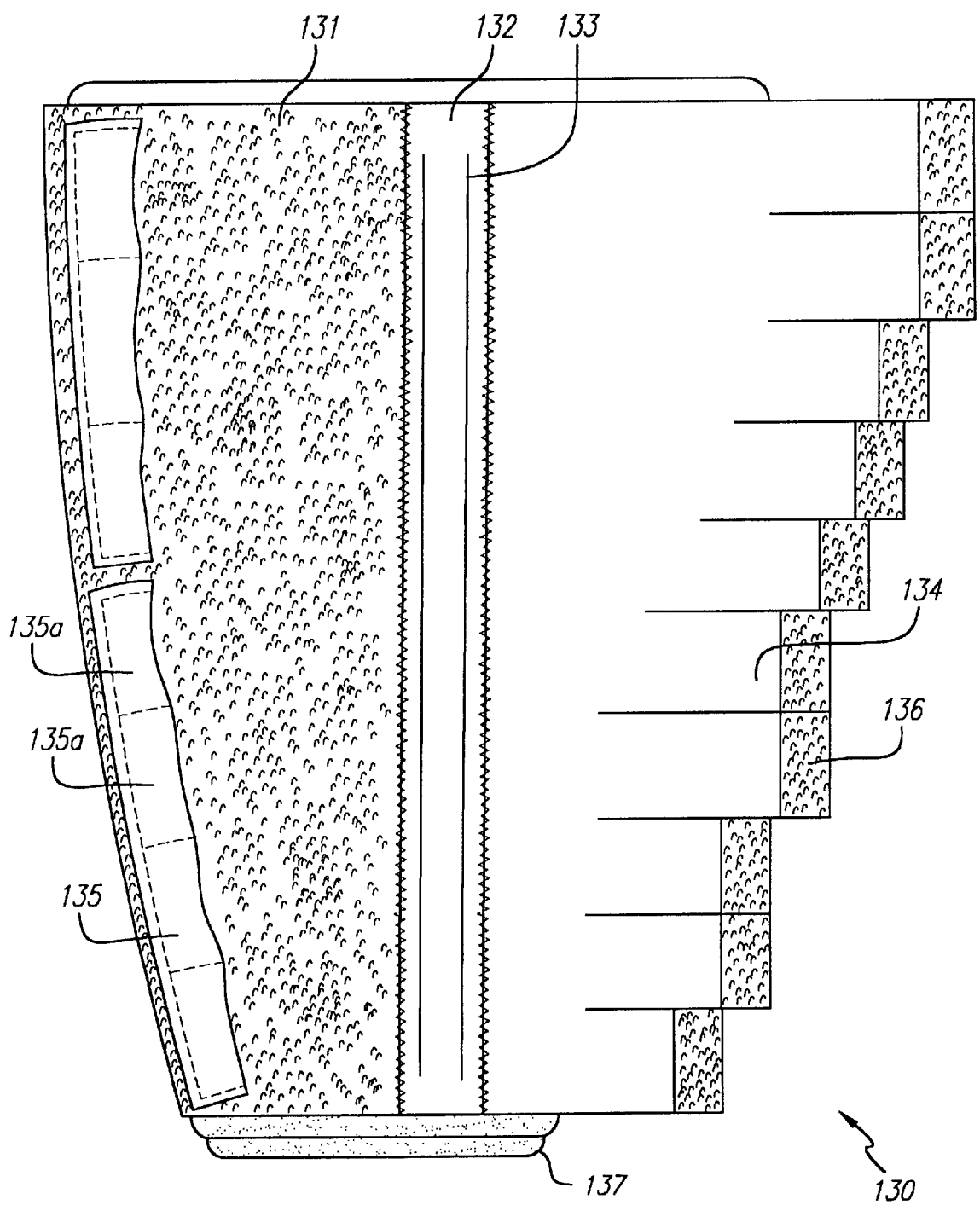
FIG. 41 is a side view of another embodiment of the compression device according to our invention.
Figure 42:
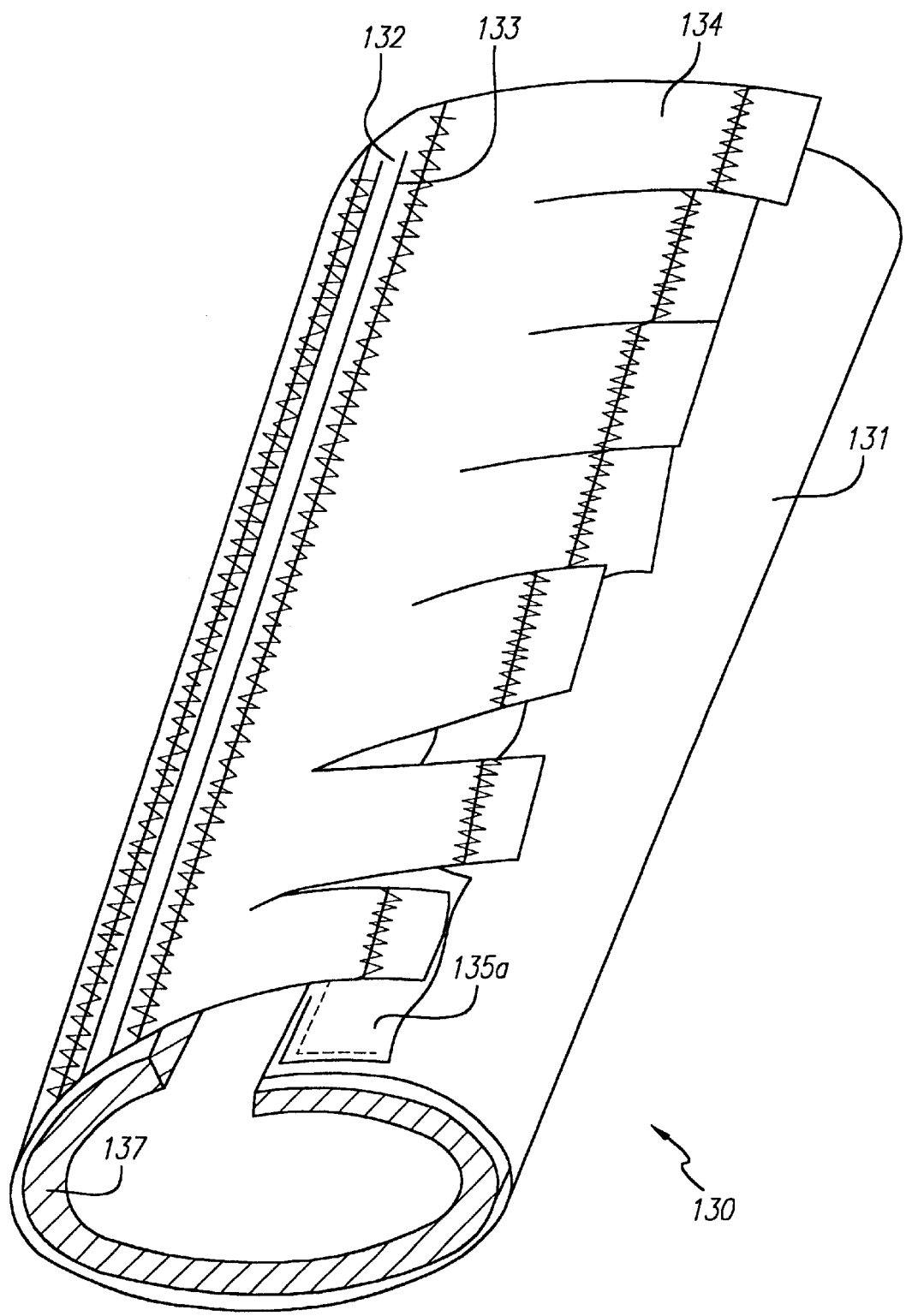
FIG. 42 is a perspective view of the compression device shown in FIG. 41.

FIGS. 41–42 show an embodiment 130 of the compression device according to our invention that is a variation of the compression device shown in FIGS. 2, 11, and 12. A large sheet 131 made of substantially inelastic material contains a band portion 132 that is elastic over the entire width of its elastic axis. The band portion 132 can be made of a Velcro-type loop material. Two or more parallel lines 133 are printed on the band portion 132 running along at least a portion of the width of the band portion 132 (transverse to the elastic axis of the band portion 132), and serve as indicia to be used with a card such as those shown in FIGS. 7–9 for determining compression. At each end of the elastic axis of the band portion 132, the band portion 132 is attached along its width to the substantially non-elastic material of the sheet 131.

The sheet 131 is divided at one or both ends into one or a plurality of sub-bands 134, which extend outwardly from the band portion 132. The lengths of the sub-bands 134 are different in order to accommodate body parts that taper or otherwise differ in circumference along their length. The sub-bands 134 can also be at angles to each other, to enable the device 130 to better conform to the body part.

At one or both ends of the device 130, pockets 135 may be sewn onto the outside surface of the device 130. The pockets 135 can be formed by folding over the edge of the sheet 131 and sewing it to itself to form pockets. Alternatively, a piece of material may be attached to the sheet 131 and then sewed along three edges, leaving one edge of the material open to form the opening of the pocket 135. Additional seams can be added to divide the pocket 135 into a series of smaller pockets 135a. In the embodiment 130, the sheet 131 is divided at one end into a series of sub-bands 134, and at the other end into a series of pockets 135a. Any combination of sub-bands 134 and pockets 135a can be used at the two ends of the sheet 131.

In use, the sheet 131 is wrapped around the body part with one or more fingers inserted into one of the pockets 135a. The user can either push his or her fingers into the sub-pocket 135a or can hook his/her fingers into the sub-pocket 135a and pull on the sub-pocket to urge the end of the sheet 131 around the body part. The device 130 is tightened around the body part by pushing or pulling the sub-pockets 135a and tucking the end of the sheet 131 having the sub-pockets 135a under the other end of the sheet 131. At the same time, one of the sub-bands 134 or a portion of the sheet 131 can be pulled over the pocket 135 and then fastened to the body of the sheet 131 using the hook fabric fasteners 136.

A padding 137, made of foam or other resilient material, may be attached to the inner side of the device 130 in order to provide protection to the body part and equally distribute the compression exerted by the device 130. The padding 137 may in some cases help to prevent the device 130 from sliding down the limb or body part by providing additional rigidity and/or a snugger fit.

The compression device 150 shown in FIG. 1 is composed of a series of bands 151 that are similar to those shown in FIGS. 24–26. The bands 151 are each joined at one end to an anchor or flexible vertical strip 156 so that the free ends 153 of the bands 151 extend outwardly from the strip 156. Each band 151 is applied by initially wrapping the band 151 only loosely, and the user observes which of the circumference markers 152 the free end 153 touches. The user then reapplies the band 151 so that the free end 153 aligns with the desired one of the compression marks 154 on the scale 155 associated with the circumference marker 152. The user then attaches the free end 153 to the surface of the band 151.

The compression marks 154 can be printed on the bands 151 such that a gradient of compression is formed when the device 150 is applied to the body. For example, the compression marks 154 on the most distal band 151 could correspond to the actual compression levels, for example 40 would correspond to 40 mm of mercury. On successively more proximal bands 151, the compression marks 154 would correspond to successively smaller percentages of the compression at the most distal of the bands 151. For example, on the second most distal of the bands 151, 40 could correspond to 36 mm of mercury, on the third most distal of the bands 151, 40 could correspond to 32 mm of mercury, and so on.

EXPLANATION OF ENGINEERING PRINCIPLES

Without limiting the present invention, the following explanation is provided to explain engineering principles used in the present invention. When wrapping a band around a limb or other material, the pressure under the band (compression) is related to the force applied to the band (tension) and the circumference of the material being wrapped, according to the following equation:

$$P = 2\pi F/(CW) \tag{1}$$

When P is pressure;

F is force in the form of tension in the band;

C is circumference; and

W is the width of the band.

The force F is assumed here to be parallel to the circumference of the body part or limb and thus perpendicular to the longitudinal axis or distal-proximal direction of the body part or limb. The force F need not have that exact direction, of course, as long as it has a component in the circumferential direction, in which case the term F as used in equations (1) and (2) refers to the circumferential component of the total force.

If a portion of the band is elastic, the stretch of the elastic is related to the force, according to the following equation:

$$S = FL/(WY) \tag{2}$$

Where S is stretch (change in length);

L is length; and

Y is a constant for a band of given thickness and composition.

The two equations (1) and (2) can be combined to cancel out force F and width W, yielding:

$$P = 2\pi YS/(CL) \tag{3}$$

If the circumference C of the body part being wrapped is known, the stretch S of a specified length L of elastic can thus be used to determine the pressure P under the band.

In practice, the relationship between force F and stretch S for a particular fabric can be determined empirically, by applying different forces F to samples of the material, and charting stretch S as a function of force F. FIGS. 43 and 44 depict and example of apparatus employed in measuring the relationship between force and stretch. FIG. 43 shows an example of a calibration test band 200 that is similar to the band 20d shown in FIG. 19, although it can have other shapes and compositions. FIG. 44 shows the band 200 mounted on a model body part P during a force/stretch calibration test.

The calibration test band 200 shown in FIG. 43 has inelastic components 201 attached to an elastic component 202. The stretch of the elastic component 202 is being measured by the apparatus shown in FIG. 44 as a function of the force generated by the known weights 203 when the calibration test band 200 is mounted on the model body part P. FIG. 45 shows an example of a chart of stretch (in inches) measured as a function of force (in pounds). The chart shows that stretch is greater for a given force when the calibration test band experiences little or no friction with the model body part P (see graph 211) compared to when friction is present (see graph 210).

The calibration of the stretch of an elastic material involves applying known amounts of force to the material and recording the stretch of that particular material. The stretch can be measured in any direction. The stretch can be measured in any reasonable units, such as inches or per cent. The elastic material can have any size, shape, or thickness while the stretch is being measured. The elastic material can take on any orientation while the stretch is being measured. For example, the material can be draped around a model leg while the stretch is being measured or the material can be layered over itself. The stretch can also be measured while the material is being used in conjunction with other materials. The elastic material can be attached to another material (elastic or not) in any manner. The force can be applied in any direction with any magnitude. For example, the force can be that of gravity. Many different forces may be applied to the elastic material at the same time while the stretch is being measured. The calibration can also be done in a way that accounts for over-stretching of the material, for example by making calibration measurements after the material has been stretched by a greater force.

The calibration should be done in a manner that mimics the actual use of the material. This is done to account for factors, like friction, which are present in the everyday application of the material. For example, if the elastic material is to be worn on a patient's leg, the calibration should be done using either a model leg or a real leg as a surface on which the material is laid. Or if the elastic material is to be layered over itself in its application, then the calibration should measure the stretch of all different layers. If the elastic material is interacting in some manner with other materials in its application, then the same materials should be present and realistically interacting with the elastic material during the calibration. The difference between the two systems of calibration (one with friction created on a model leg and the other without friction) is evident in FIG. 44. The system of calibration to use depends upon the application.

The data compiled in the calibration can be manipulated in many physical applications. For instance, the applied force can be converted into a measurement of pressure. This can be done when the material is wrapped around a surface and enables the calculation of applied compression from a measurement of stretch.

EXAMPLE

A clinical trial was conducted to test the efficacy of the arm-sleeve embodiment (FIGS. 2 and 10–12) of the present invention. Four individuals participated. Each of these persons had previously had his or her arms bandaged and had used another type of therapeutic compression garment.

An open-ended woven protective garment ("stockinet") was first put on the bare arm ensuring that the stockinet was not bunched up or folded in any way. The stockinet was cut to fit the limb correctly. Then a foam pad 29 was wrapped around the top of the arm under the arm-sleeve taking care that, similarly, it not be folded or twisted. The foam pad 29 was added for protection and comfort of the patient. Finally, the arm-sleeve embodiment 20 was put on over the foam pad 29.

Starting at the distal end, or the end nearest the hand, the first sub-band 27 was tightened around the arm by lifting up the hook fastener 28 by its loose end, pulling the fastener 28 so as to tighten the arm-sleeve 24, and re-attaching the fastener 28 back down to the looped surface sheet 21 of the sleeve 24.

Before tightening the remaining fasteners 28 proximally towards the shoulder, the hand wrap 30 was then wrapped around the hand, when appropriate. Using moderate tension, four turns were made around the hand, first once passing under the thumb, then once around the palm, then once under the thumb again and finally around the palm again. Any excess length was cut off and the end 32 of the hand wrap 30 was attached to the distal end 31 of the sleeve 24 with the hook material fastener 33.

The remaining sub-bands 27 were then fastened and tightened in the same manner as the sub-band 27 nearest the wrist until the last sub-band 27 was fastened and tightened nearest the shoulder. Once all the sub-bands were tightened, the circumference of the wrist over the arm-sleeve 24 was measured. Referring to the compression card 7b, the patient's size was determined according to the following chart:

| CIRCUMFERENCE OF WRIST AS MEASURED OVER THE ARM-SLEEVE | SIZE |
| --- | --- |
| 6"–8" | Small |
| 8"–10" | Medium |
| 10"–13" | Large |
| 13"–16" | Extra Large |

The compression measuring card 7b was then laid across the inside of the arm-sleeve 24 over the indicia lines 25 on the elastic strip 23, in order to position the reference mark 11 over one of the indicia lines 25 of the elastic strip 23 and read where the other indicia line 25 intersected the scale 12b on the compression measuring card 7b. This reading gave the measure of the compression underneath the arm-sleeve at the wrist.

A therapist or physician had previously advised each patient of his or her appropriate level of compression. Each patient then adjusted the tightness of the sub-band 27 nearest the wrist to obtain the prescribed compression, using the card 7b to read the compression level as described before.

Proceeding up the limb, the user applied the same amount of tension as was used on the first sub-band 27. Consistent pressure was obtained by using the compression card 7b as each sub-band 27 was tightened. For each sub-band 27, the reference mark 11 for the same edge 8b of the card 7b as at the first sub-band 27 was placed on one of the indicia lines 25 printed on the elastic strip 23. The fastener 28 was then tightened so that the other indicia line 25 corresponded with the same one of the compression level markings 12b. As a result the tension provided by the elastic strip 23 was constant at any point up the arm. This resulted in an automatic gradient of compression because of the natural taper of the arm.

The patients universally reported that this arm-sleeve product 20 provided greater all-around comfort, was easier to use and was not as cumbersome as other products. Participants reported reduction in swelling, most noticeably in the wrist and elbow. Some also noticed softening of the arm tissue that had been hardened by their underlying circulatory disorder.

Accordingly, the reader will see that the compression devices with compression measuring systems of this invention allow the user to accurately and reliably predict and measure compression levels. Furthermore, the compression devices with compression measuring systems have the additional advantages in that the user may accurately and reliably apply pre-selected compression levels;
  the user may quickly change the compression levels being applied by the devices to different compression levels;
  the user may accurately and conveniently change the compression levels being applied by the devices to the different compression levels required by different postures of the user;
  the user may accurately and conveniently change the compression levels being applied by the devices to the different compression levels required by diurnal changes;
  the user may quickly change the compression levels being applied by the devices without having to remove the devices from the body part or limb;
  the user may set a consistent tension in all parts of the device in order to create an automatic distal-proximal compression gradient along the body part;
  the user will find that the compression devices are comfortable to wear;
  the user can easily apply and remove the compression devices to and from parts of the body;
  the user can measure the circumferences of the body part with the circumference measuring systems integral to the devices;
  the user will be able to easily tighten the devices when setting the compression to be applied, even if the hands of the user are disabled; and
  the user may accurately and conveniently adjust the devices to account for swelling or reduction in the limb volume.

Readers of skill in the art to which this invention pertains will understand that the foregoing description of the details of preferred embodiments is not to be construed in any manner as to limit the invention. Such readers will understand that other embodiments may be made which fall within the scope of the invention, which is defined by the following claims and their legal equivalents.

We claim:

1. A therapeutic garment for applying compression to a part of the body and having a system for measuring compression, comprising:
   (a) a flexible sleeve having an outer surface and an inner surface for wrapping at least partially around the body part, at least a portion of the sleeve being made of an elastic material so that the sleeve will stretch along an elastic axis around the body part, the outer surface bearing indicia printed thereon wherein measurement of a position of at least one of the indicia relative to a reference position on the outer surface provides a measurement of the stretch of the elastic material; and
   (b) a card having a scale for measuring the separation of the position of the at least one indicia from the reference position and providing the compression level for the pre-measured circumference of the body part in order to determine the actual compression provided by the sleeve and adjusting the compression provided by the sleeve accordingly.

2. The garment according to claim 1 in which the sleeve further comprises at least one portion of flexible and inelastic material attached to the portion made of elastic material.

3. The garment according to claim 2 in which at least one side of the portion of flexible and inelastic material is cut along a curve before being attached to the portion of elastic material so that the sleeve is biased into a three-dimensional curvature in order to fit the body part.

4. The garment according to claim 1 in which substantially the entire sleeve is made of elastic material.

5. The garment according to claim 1 further comprising means for attaching a free end of the sleeve to the outer surface of the sleeve when the sleeve is placed around the body part in order to tighten and secure the sleeve.

6. The garment according to claim 1 in which the sleeve is comprised in part of an inelastic material.

7. The garment according to claim 6 in which sub-bands are defined in the inelastic material by one or more circumferentially extending slits and further comprising means for removably attaching a folded over portion of each sub-band to the outer surface of the sleeve.

8. The garment according to claim 1 further comprising:
   (a) a plurality of pairs of straps attached to the sleeve and extending outwardly in opposite directions from both sides of the sleeve to encompass the body part; and
   (b) means for fastening each of the straps to the other of its pair or to the sleeve, whereby the opposite straps of each pair of straps can be extended toward each other and at least one strap of each pair can be tightened to stretch the elastic material of the sleeve and thereby compress the body part.

9. The garment according to claim 8 in which the straps are made of inelastic material and the sleeve is substantially comprised of the elastic material.

10. The garment according to claim 8 in which one of each pair of opposed straps has a hole defined therein for receiving the other of the pair of straps in threaded engagement and each strap has a fastener surface for removable attachment to the outer surface of the sleeve.

11. The garment according to claim 8 in which one of each pair of opposed straps has a ring attached for receiving an end of the other of the straps therethrough in folded relationship so that the end can be pulled away from the ring in order to tighten the sleeve and further comprising a fastener surface attached to the end for attaching the end to the outer surface of the sleeve.

12. The garment according to claim 1 further comprising a pocket attached to the garment adjacent at least an end of the garment, the pocket having a compartment sized to admit at least one finger inserted through an opening in the pocket that faces in a direction substantially away from the end of the garment, whereby a person can urge the end of the garment around the body part by inserting at least one finger through the opening into the compartment of the pocket and pushing or pulling with the at least one finger toward the end of the garment.

13. The garment according to claim 1 further comprising padding disposed on said inner surface of said flexible sleeve.

14. The garment according to claim 13 in which the sleeve further comprises at least one portion of flexible and inelastic material attached to the portion made of elastic material.

15. The garment according to claim 14 in which at least one side of the portion of flexible and inelastic material is cut along a curve before being attached to the portion of elastic material so that the sleeve is biased into a three-dimensional curvature in order to fit the body part.

16. The garment according to claim 13 in which substantially the entire sleeve is made of elastic material.

17. The garment according to claim 13 further comprising means for attaching a free end of the sleeve to the outer surface of the sleeve when the sleeve is placed around the body part in order to tighten and secure the sleeve.

18. The garment according to claim 13 in which the sleeve is comprised in part of an inelastic material.

19. The garment according to claim 18 in which subbands are defined in the inelastic material by one or more circumferentially extending slits and further comprising means for removably attaching a folded over portion of each sub-band to the outer surface of the sleeve.

20. The garment according to claim 13 further comprising:
(a) a plurality of pairs of straps attached to the sleeve and extending outwardly in opposite directions from both sides of the sleeve to encompass the body part; and
(b) means for fastening each of the straps to the other of its pair or to the sleeve, whereby the opposite straps of each pair of straps can be extended toward each other and at least one strap of each pair can be tightened to stretch the elastic material of the sleeve and thereby compress the body part.

21. The garment according to claim 20 in which the straps are made of inelastic material and the sleeve is substantially comprised of the elastic material.

22. The garment according to claim 20 in which one of each pair of opposed straps has a hole defined therein for receiving the other of the pair of straps in threaded engagement and each strap has a fastener surface for removable attachment to the outer surface of the sleeve.

23. The garment according to claim 20 in which one of each pair of opposed straps has a ring attached for receiving an end of the other of the straps therethrough in folded relationship so that the end can be pulled away from the ring in order to tighten the sleeve and further comprising a fastener surface attached to the end for attaching the end to the outer surface of the sleeve.

24. The garment according to claim 20 further comprising a pocket attached to the garment adjacent at least an end of the garment, the pocket having a compartment sized to admit at least one finger inserted through an opening in the pocket that faces in a direction substantially away from the end of the garment, whereby a person can urge the end of the garment around the body part by inserting at least one finger through the opening into the compartment of the pocket and pushing or pulling with the at least one finger toward the end of the garment.

25. A therapeutic garment for applying compression to a part of the body and having a system for measuring compression, comprising:
(a) a plurality of flexible sleeves attached to each other, the sleeves each having an outer surface and an inner surface for wrapping at least partially around the body part, at least a portion of the sleeves being made of an elastic material so that the sleeves will stretch along an elastic axis around the body part, the outer surface bearing indicia printed thereon wherein measurement of a position of at least one of the indicia relative to a reference position on the outer surface provides a measurement of the stretch of the elastic material; and
(b) a card having a scale for measuring the separation of the position of the at least one indicia from the reference position and providing the compression level for the pre-measured circumference of the body part in order to determine the actual compression provided by the sleeves and adjusting the compression provided by the sleeves.

26. The garment according to claim 25 in which the sleeves are each attached to an anchor at an end of each of the sleeves.

27. The garment according to claim 25 in which the sleeves are sewn to each other.

28. The garment according to claim 25 further comprising a pocket attached to the garment adjacent at least an end of the garment, the pocket having a compartment sized to admit at least one finger inserted through an opening in the pocket that faces in a direction substantially away from the end of the garment, whereby a person can urge the end of the garment around the body part by inserting at least one finger through the opening into the compartment of the pocket and pushing or pulling with the at least one finger toward the end of the garment.

29. The garment according to claim 25 further comprising padding disposed on said inner surface of said flexible sleeve.

30. The garment according to claim 29 in which the sleeves are each attached to an anchor at an end of each of the sleeves.

31. The garment according to claim 29 in which the sleeves are sewn to each other.

32. The garment according to claim 29 further comprising a pocket attached to the garment adjacent at least an end of the garment, the pocket having a compartment sized to admit at least one finger inserted through an opening in the pocket that faces in a direction substantially away from the end of the garment, whereby a person can urge the end of the garment around the body part by inserting at least one finger through the opening into the compartment of the pocket and pushing or pulling with the at least one finger toward the end of the garment.

33. A garment for providing compression to a body part, comprising:
(a) a first portion having inner and outer surfaces, said first portion comprising elastic material and having first and second edges that are substantially parallel;
(b) a second portion made of flexible and non-elastic material that has a first side cut into a curve related to the circumferences of the body part to be encompassed by the garment such that a longitudinal dimension of the second portion between the first and second edges of the second portion is smaller where the body part has a smaller circumference and is larger where the body part has a larger circumference, the first edge of the second portion being attached to one of the first and second edges of the first portion so that the second portion is biased into a three-dimensional curvature to fit the body part;
(c) a third portion made of flexible and non-elastic material that has a first side cut into a curve related to the circumferences of the body part to be encompassed by the garment such that a longitudinal dimension of the third portion between the first and second edges of the third portion is smaller where the body part has a smaller circumference and is larger where the body part has a larger circumference, the first edge of the third portion being attached to the other of the first and second edges of the first portion so that the third portion is biased into a three-dimensional curvature to fit the body part; and
(d) means for detachably securing the second portion to the third portion so as to encircle the body part and to draw the second portion to the third portion to stretch the first portion and thereby provide a tension in the garment that will compress the body part.

34. The garment according to claim 33 further comprising:
(a) indicia printed on said outer surface wherein measurement of a position of at least one of the indicia relative to a reference position on the outer surface provides a measurement of the stretch of the elastic material; and (b) a card having a scale for measuring the separation of the position of the at least one indicia from the reference position and providing a compression level for a pre-measured circumference of the body part in order to determine the actual compression provided by the garment and adjusting the compression provided by the garment accordingly.

35. The garment according to claim 33 further comprising a pocket attached to the garment adjacent at least an end of the garment, the pocket having a compartment sized to admit at least one finger inserted through an opening in the pocket that faces in a direction substantially away from the end of the garment, whereby a person can urge the end of the garment around the body part by inserting at least one finger through the opening into the compartment of the pocket and pushing or pulling with the at least one finger toward the end of the garment.

36. The garment according to claim 33 further comprising padding disposed on said inner surface of said flexible sleeve.

37. The garment according to claim 36 further comprising:

(a) indicia printed on said outer surface wherein measurement of a position of at least one of the indicia relative to a reference position on the outer surface provides a measurement of the stretch of the elastic material; and (b) a card having a scale for measuring the separation of the position of the at least one indicia from the reference position and providing a compression level for a pre-measured circumference of the body part in order to determine the actual compression provided by the garment and adjusting the compression provided by the garment accordingly.

38. The garment according to claim 36 further comprising a pocket attached to the garment adjacent at least an end of the garment, the pocket having a compartment sized to admit at least one finger inserted through an opening in the pocket that faces in a direction substantially away from the end of the garment, whereby a person can urge the end of the garment around the body part by inserting at least one finger through the opening into the compartment of the pocket and pushing or pulling with the at least one finger toward the end of the garment.

39. A therapeutic garment for applying compression to a part of the body and having a system for measuring compression, comprising:

(a) a sleeve having an inner surface and an outer surface, said sleeve for wrapping around the body part in a longitudinal direction of the band, the sleeve having a portion made of an elastic material so that the sleeve can be stretched in the longitudinal direction of the sleeve in order to compress the body part, the elastic material portion of the sleeve having indicia thereon for indicating the amount of the compression provided to the body part by the sleeve for a plurality of circumferences of the body part; and (b) a card having at least two edges, each edge having marks for measuring the distance between successive indicia on the elastic material of the sleeve and stating the compression provided corresponding to the measured distance, wherein the marks on each edge are for a different circumference or pressure of the body part.

40. The garment according to claim 39 further comprising a pocket attached to the garment adjacent at least an end of the garment, the pocket having a compartment sized to admit at least one finger inserted through an opening in the pocket that faces in a direction substantially away from the end of the garment, whereby a person can urge the end of the garment around the body part by inserting at least one finger through the opening into the compartment of the pocket and pushing or pulling with the at least one finger toward the end of the garment.

41. The garment according to claim 39 further comprising padding disposed on said inner surface of said sleeve.

42. A therapeutic garment for applying compression to a part of the body and having a system for measuring compression, comprising:

(a) a band comprising an elastic material so that the band provides a tensioning force along an elastic axis of the elastic material in a longitudinal direction of the band when the band is stretched around at least a portion of the object in order to compress the object; and (b) a system for indicating the level of the compression provided to the object by the band comprising means for measuring the stretch of the elastic material and means for indicating the compression level corresponding to the measured stretch and the circumference of the portion of the object.

43. The garment according to claim 42 in which the means for measuring comprises a plurality of indicia printed on the band.

44. The garment according to claim 43 in which the indicia are printed on the elastic material.

45. The garment according to claim 43 in which the indicia are spaced from each other in the longitudinal direction.

46. The garment according to claim 42 further comprising means for measuring the circumference of the portion of the object.

47. The garment according to claim 43 in which the means for measuring comprises a card having at least one edge with a reference mark and a measurement scale having one or more measurement marks for measuring an amount of the separation of a pair of the indicia selected so that at least a portion of the elastic material separates the members of the selected pair of indicia in the direction of the elastic axis and the means for indicating comprises legends printed on the card adjacent the measurement scale that correlates the one or more measurement marks with one or more compression levels for a given circumference of the portion of the object.

48. The garment according to claim 42 in which the means for measuring comprises at least one measurement scale printed on the band comprising one or more measurement marks for measuring a position of a free end of the band.

49. The garment according to claim 47 in which the means for indicating comprises legends printed on the band adjacent the measurement scale that correlates the one or more measurement marks with one or more compression levels for a given circumference of the body part.

50. The garment according to claim 42 in which the means for measuring and the means for indicating comprise a plurality of indicia printed on the band and spaced apart from each other along the longitudinal direction.

51. The garment according to claim 42 in which the band is formed so as to overlappingly wrap around the object and further comprising means for fastening a free end of the band to another portion of the band in order to retain the band stretched around the object.

52. The garment according to claim 42 in which the band is formed as a garment to encompass at least a portion of a body part.

53. A method for treating a medical disorder that requires compression therapy, the method comprising the steps of applying to an indicated body part the band of claim 42 and using the system of claim 42 for indicating the level of compression to set a pre-determined compression level to the indicated body part.

54. A therapeutic garment for applying compression to a part of the body and having a system for measuring compression, comprising a band for providing therapeutic compression to a body part, the band being comprised at least in part of elastic material and being capable of being stretched along an elastic axis of the elastic material that coincides with a longitudinal direction of the band, the band having at least one scale located thereon, the at least one scale comprising a set of markings each of which corresponds to a compression for a given circumference of the body part, and the markings are so located that the position of an edge or other specified portion of a free end of the band with respect to the markings when the band is wrapped and tightened in its longitudinal direction around the body part indicates the stretch of the band and the markings will indicate the corresponding compression provided to the body part by the band for a pre-measured circumference of the body part.

55. The garment according to claim 54 in which the given circumference is the same for each of the markings in a scale and each of the markings in the scale corresponds to a different compression.

56. The garment according to claim 54 in which the compression is the same for each of the markings in a scale and each of the markings in the scale corresponds to a different circumference.

57. The garment according to claim 54 further comprising circumference measurement markings located on the band at positions corresponding to the position of the free end of the band for different circumferences of the body part when the band is wrapped but not tightened around the body part.

58. A method for applying therapeutic compression to a body part, comprising the following steps:
   a. measuring a circumference of the body part;
   b. placing a therapeutic garment comprising a band comprised at least in part of an elastic material around the body part;
   c. tensioning the band so that the band provides compression to the body part; measuring the stretch of the elastic material;
   d. selecting a compression scale appropriate to the measured circumference of the body part; and
   e. reading the compression scale to determine the compression provided to the body part.

\* \* \* \* \*